United States Patent
Kuhlmann et al.

(10) Patent No.: US 10,066,662 B2
(45) Date of Patent: Sep. 4, 2018

(54) BEARING FOR SUPPORTING A SHAFT, IN PARTICULAR A RUDDER SHAFT, OR A RUDDER BLADE, ELECTRONIC BEARING CLEARANCE MEASURING DEVICE, RUDDER COMPRISING A BEARING FOR SUPPORTING A SHAFT OR A RUDDER BLADE, AND METHOD FOR MEASURING WEAR OF A BEARING FOR SUPPORTING A SHAFT OR A RUDDER BLADE

(71) Applicant: becker marine systems GmbH & Co. KG, Hamburg (DE)

(72) Inventors: Henning Kuhlmann, Hamburg (DE); Leif Seliger, Kiel (DE)

(73) Assignee: becker marine systems GmbH & Co. KG, Hamburg (DE)

( * ) Notice: Subject to any disclaimer, the term of this patent is extended or adjusted under 35 U.S.C. 154(b) by 0 days.

(21) Appl. No.: 15/300,448

(22) PCT Filed: Mar. 27, 2015

(86) PCT No.: PCT/EP2015/056738
§ 371 (c)(1),
(2) Date: Sep. 29, 2016

(87) PCT Pub. No.: WO2015/150266
PCT Pub. Date: Oct. 8, 2015

(65) Prior Publication Data
US 2017/0122366 A1    May 4, 2017

(30) Foreign Application Priority Data

Apr. 1, 2014 (DE) .......... 10 2014 104 608
Jul. 23, 2014 (DE) .......... 10 2014 110 383

(51) Int. Cl.
*F16C 17/24* (2006.01)
*B63H 25/38* (2006.01)
(Continued)

(52) U.S. Cl.
CPC ........... *F16C 17/246* (2013.01); *B63H 25/38* (2013.01); *B63H 25/52* (2013.01); *F16C 17/02* (2013.01);
(Continued)

(58) Field of Classification Search
CPC ........ B63H 25/00; B63H 25/06; B63H 25/38; B63H 25/381; B63H 25/52; B63H 25/08; F16C 17/02; F16C 17/246
(Continued)

(56) References Cited

U.S. PATENT DOCUMENTS 3,102,759 A    9/1963  Stewart
3,775,680 A    11/1973 Egeland
(Continued)

FOREIGN PATENT DOCUMENTS

CN    1891571 A      1/2007
CN    101380996 A    3/2009
(Continued)

*Primary Examiner* — Lars A Olson
(74) *Attorney, Agent, or Firm* — Kelly & Kelley, LLP

(57) ABSTRACT

The invention relates to a bearing for supporting a shaft, in particular a rudder shaft, or a rudder blade, by means of which bearing the bearing clearance or the bearing wear can be continuously monitored, determined, and optionally documented. According to the invention, for a bearing for supporting a shaft, in particular a rudder shaft, comprising a first bearing element and a second bearing element, wherein the first bearing element has a sliding surface for contacting the second bearing element in a sliding manner, and a measurement-value sensor having a wear surface for con-
(Continued)

Figure 1:
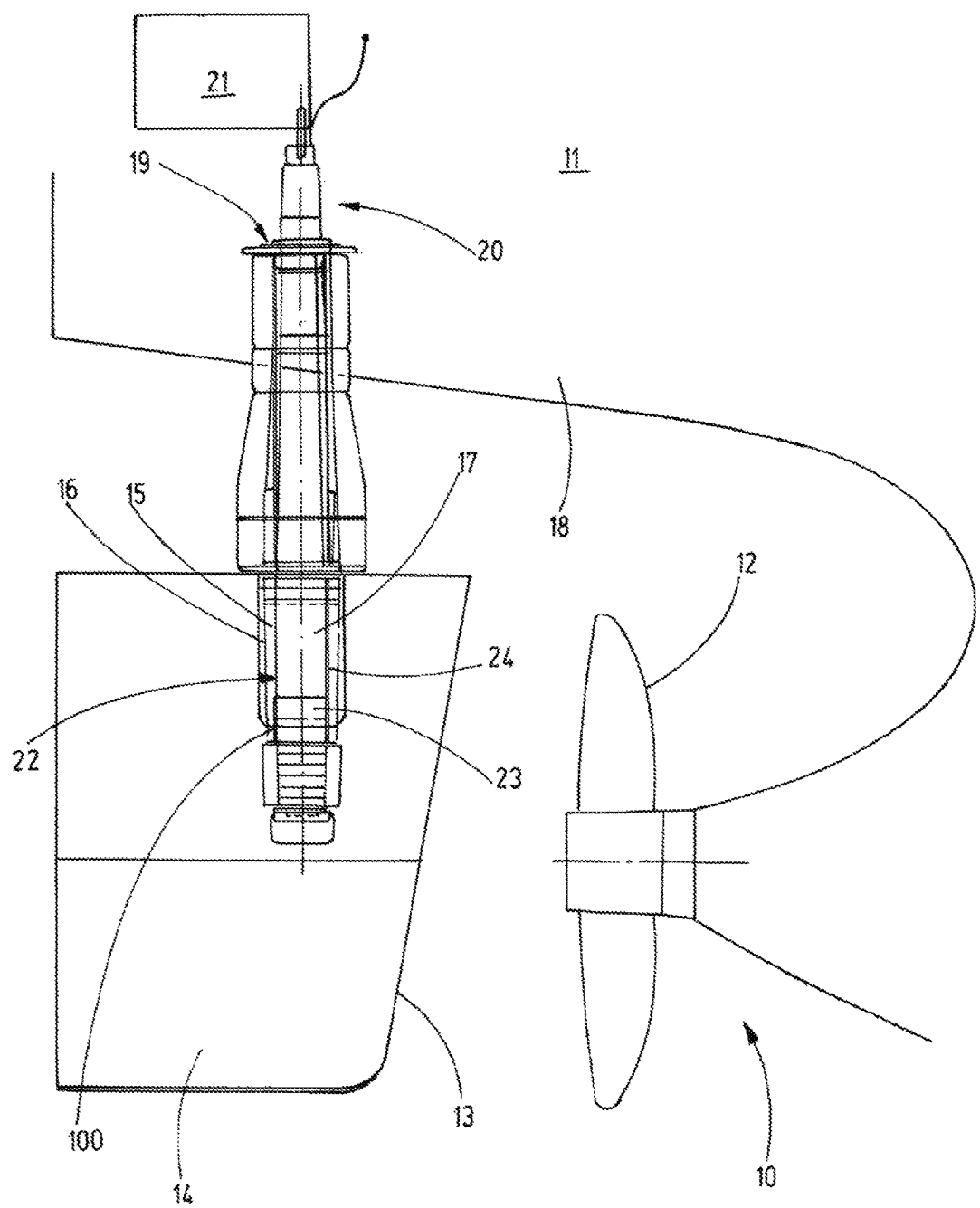

tacting the second bearing element in a sliding manner, the at least one measurement-value sensor is not pin-shaped.

20 Claims, 10 Drawing Sheets

(51) Int. Cl.
*B63H 25/52* (2006.01)
*F16C 17/02* (2006.01)
*G01N 3/56* (2006.01)
*G01B 5/14* (2006.01)
*G01B 7/14* (2006.01)

(52) U.S. Cl.
CPC ............ *G01B 5/146* (2013.01); *G01B 7/144* (2013.01); *G01N 3/56* (2013.01); *F16C 2233/00* (2013.01); *F16C 2326/30* (2013.01)

(58) Field of Classification Search
USPC .................................................. 114/162, 169
See application file for complete search history.

(56) References Cited

U.S. PATENT DOCUMENTS

| | | | |
|---|---|---|---|
| 4,024,827 A * | 5/1977 | Becker | ................ B63H 25/381 114/162 |
| 5,701,119 A | 12/1997 | Jurras, III | |
| 7,509,918 B2 * | 3/2009 | Lehmann | ............... B63H 25/38 114/162 |
| 7,516,559 B2 | 4/2009 | Kluge et al. | |
| 7,523,670 B2 | 4/2009 | Meyer et al. | |
| 7,591,230 B2 * | 9/2009 | Kluge | .................... B63H 25/38 114/162 |
| 7,677,079 B2 | 3/2010 | Radziszewski et al. | |
| 2009/0223083 A1 | 9/2009 | LeCrone | |

FOREIGN PATENT DOCUMENTS

| | | |
|---|---|---|
| CN | 102844236 A | 12/2012 |
| DE | 21 15 506 B | 8/1974 |
| DE | 10 2009 046 162 A1 | 5/2011 |
| DE | 10 2011 002 832 A1 | 7/2012 |
| EP | 1 602 842 A1 | 12/2005 |
| EP | 1 780 118 A2 | 5/2007 |
| GB | 2 192 949 A | 1/1988 |
| KR | 10-2010-0136590 A | 12/2010 |
| KR | 10-2012-0118117 A | 10/2012 |
| WO | 2003/025407 A2 | 3/2003 |
| WO | 2005/083411 A1 | 9/2005 |
| WO | 2011/051388 A1 | 5/2011 |
| WO | 2011/117301 A1 | 9/2011 |
| WO | 2012/098150 A1 | 7/2012 |

* cited by examiner

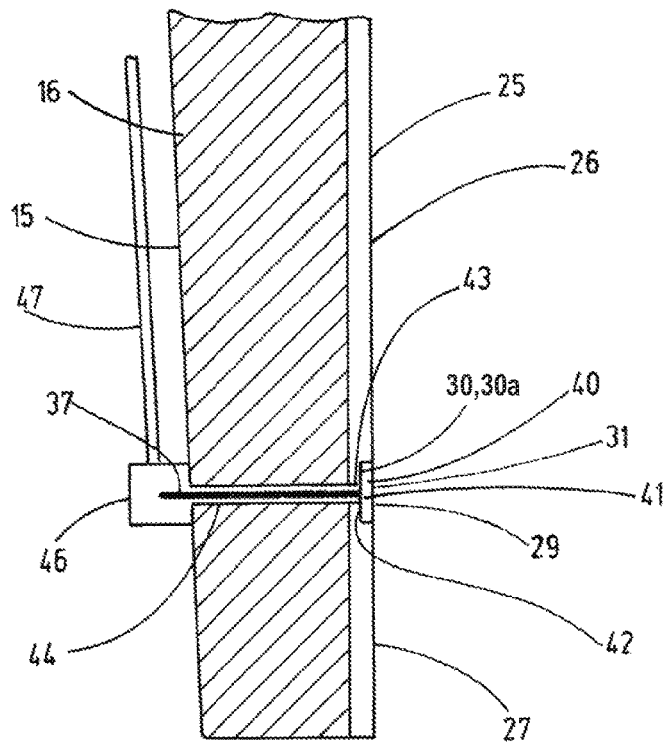
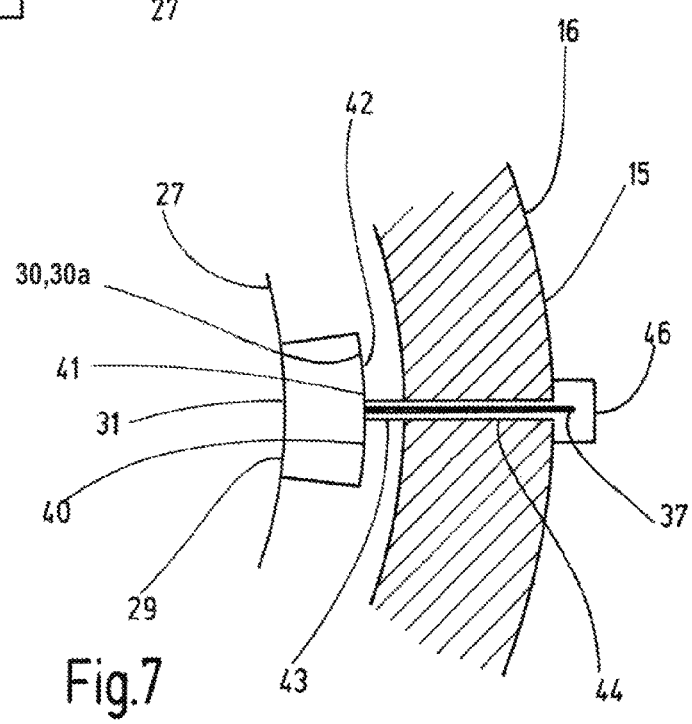

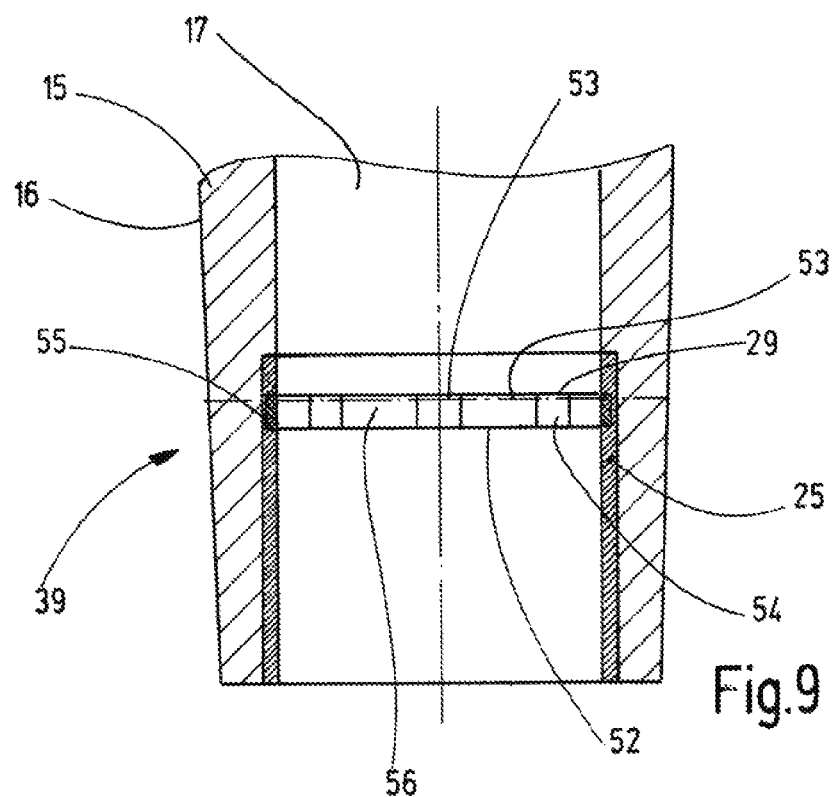
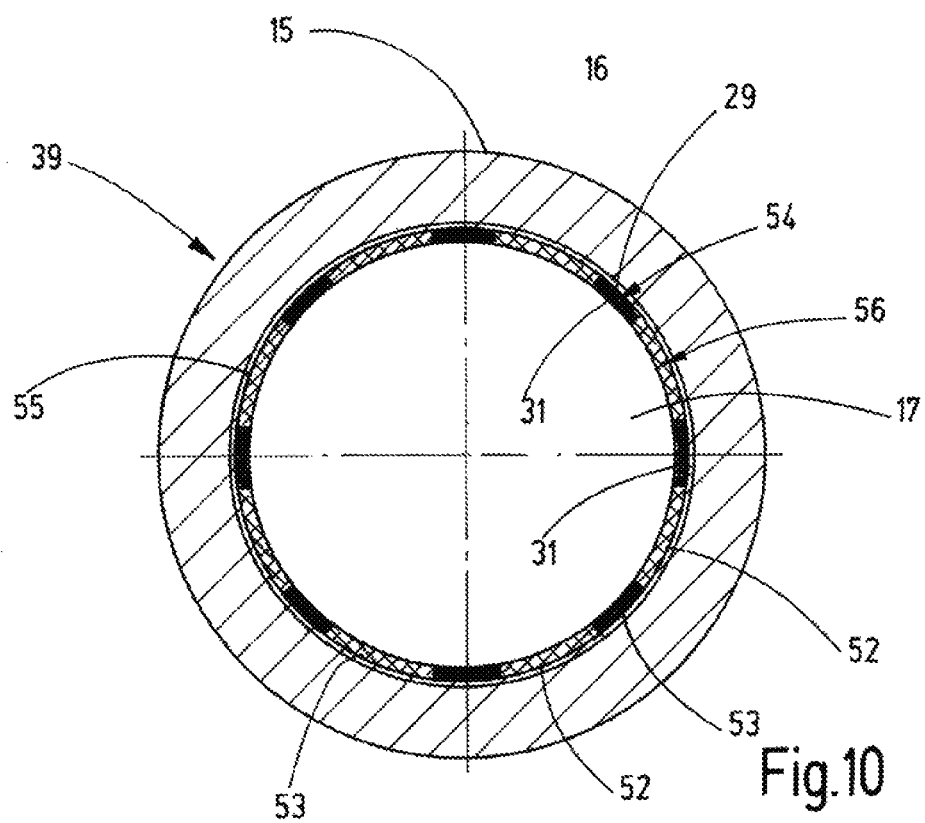

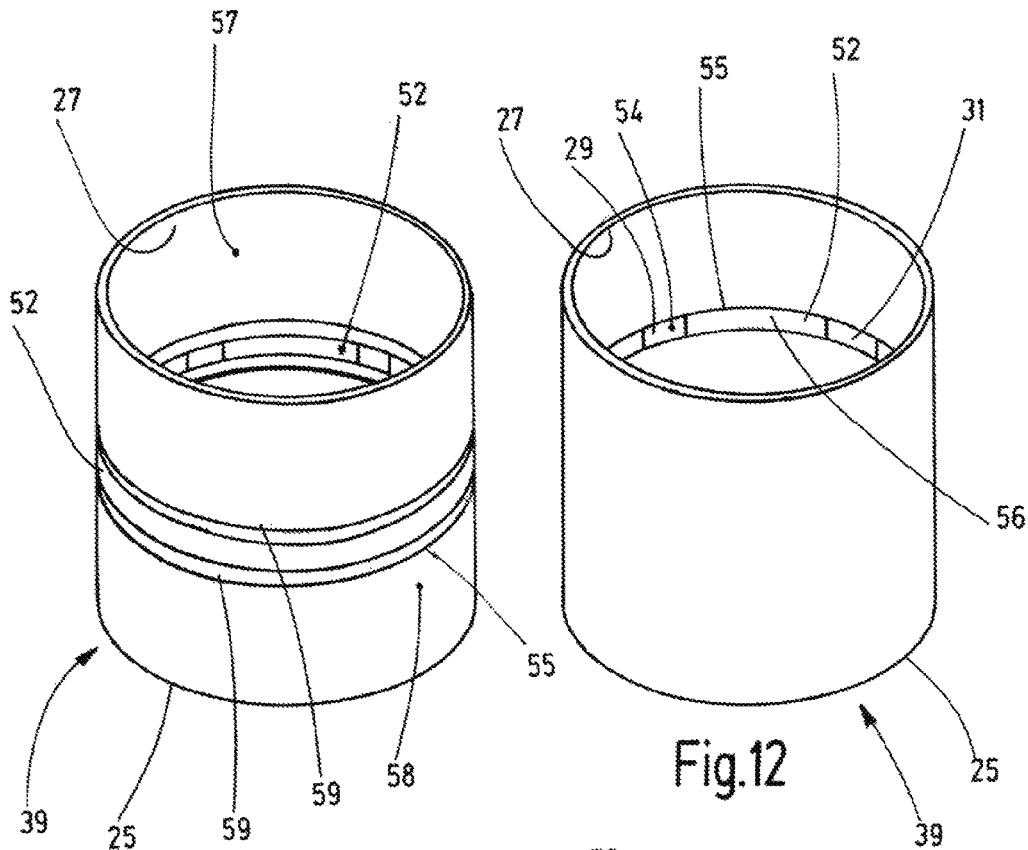
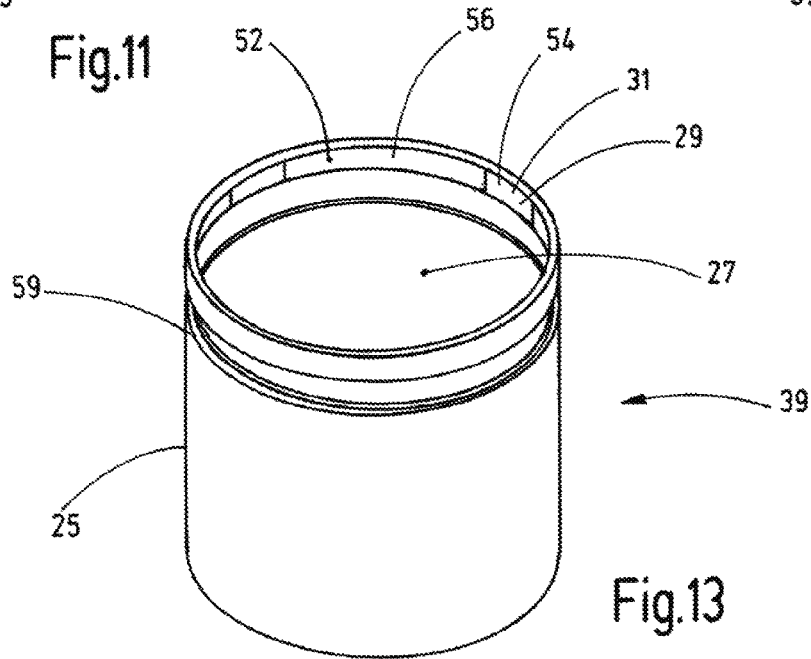

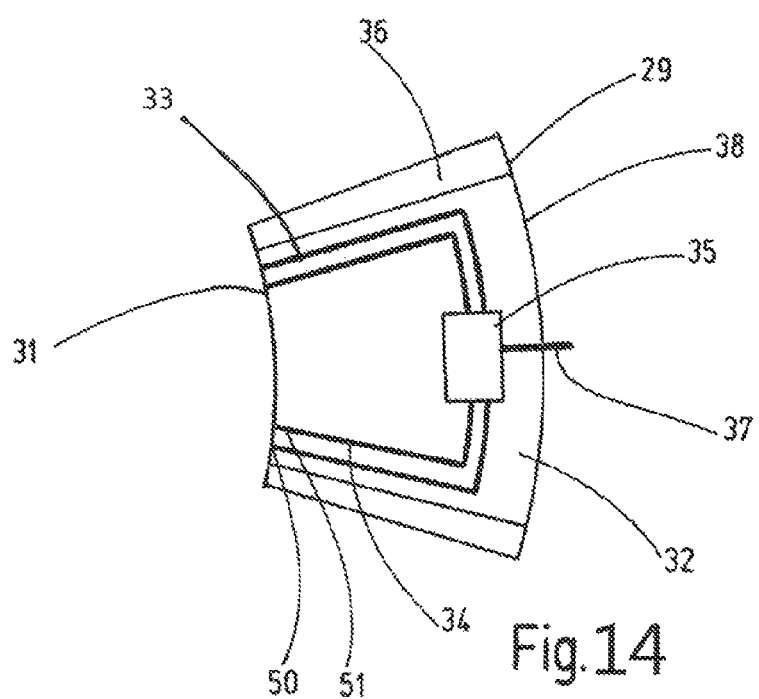

BEARING FOR SUPPORTING A SHAFT, IN PARTICULAR A RUDDER SHAFT, OR A RUDDER BLADE, ELECTRONIC BEARING CLEARANCE MEASURING DEVICE, RUDDER COMPRISING A BEARING FOR SUPPORTING A SHAFT OR A RUDDER BLADE, AND METHOD FOR MEASURING WEAR OF A BEARING FOR SUPPORTING A SHAFT OR A RUDDER BLADE

The invention relates to a bearing for supporting a shaft or a rudder blade, comprising a first bearing element and a second bearing element, wherein the first bearing element has a sliding surface for contacting the second bearing element in a sliding manner, and a measurand sensor having a wear surface for contacting the second bearing element in a sliding manner. The invention also relates to a bearing clearance measuring device, a rudder comprising a bearing for supporting a shaft or a rudder blade, and a method for measuring the wear of a bearing for supporting a shaft or a rudder blade.

In the case of large rudders, for example for container ships, it is known that the rudder shaft is introduced far into the interior of the rudder blade by means of a rudder trunk, when the rudder is designed as a full spade rudder. In general, the rudder shaft at the free end of the rudder trunk is mounted in a journal bearing which is arranged between the rudder trunk and rudder shaft and which is designed for example as a plain bearing. The plain bearings can be arranged alternatively or additionally also at other positions between the rudder trunk and rudder shaft. A journal or other plain bearing can also be arranged between the rudder trunk and rudder blade, that is to say placed on the outer side of the rudder trunk. Such or similar plain bearings can also be used, however, for supporting shafts, for example. Such or similar bearings are used especially in the case of propeller shafts of large container ships.

Over the course of use, the bearing becomes worn, and therefore a very complicated exchange of the bearing must be carried out, in which the rudder blade and/or the propeller must be removed from the rudder shaft and/or propeller shaft respectively.

PRIOR ART

EP 1 780 118 B1 discloses a device with a handle for measuring the journal bearing clearance to check how far the wear of the bearing has progressed. The device can be inserted via a flap in the rudder blade, for example by a diver, into the bearing, so that the journal bearing clearance and thus the wear of the bearing can be measured without a removal of the rudder blade.

WO 2011/117301 A1 discloses a rudder for ships comprising at least one bearing for supporting a rudder blade or rudder shaft on the ship's hull. The bearing has an inner bearing portion and an outer bearing portion resting against the inner bearing portion in a sliding manner. A wear pin is arranged on the outer bearing portion or on the inner bearing portion, which rests against the other of the inner bearing portion and outer bearing portion in a sliding manner. The wear pin is inserted from the outside into a through-hole of the outer bearing portion and passes through this so that it contacts the inner bearing portion in a sliding manner. The wear pin can be removed from the outside of the outer bearing portion.

This gives rise in the aforementioned prior art to the problem that the known wear pin is vulnerable with respect to shear forces and thus there is a risk of damage to the wear pin as a result of friction and shearing forces occurring with sliding contact of the wear pin against an inner bearing portion.

Furthermore, there is the problem that the wear pin arranged in the through-hole can have play therein, in particular radial play, which may mean that the wear pin is not continuously arranged slidingly on the inner bearing portion, and bearing wear cannot be reliably measured. Further, due to the relatively large dimensions of the through-hole, as this has to receive the wear pin, a structural weakening of the outer bearing portion can occur.

DISCLOSURE OF THE INVENTION: OBJECT, SOLUTION, ADVANTAGES

The object of the invention is to solve the specified problems and to provide a bearing for mounting a shaft, in particular a rudder shaft, or a rudder blade, with which bearing the bearing clearance or the bearing wear can be continuously monitored, determined, and optionally documented. This object is achieved by the bearing according to the invention for supporting a shaft, in particular a rudder shaft, or a rudder blade. The object is also achieved by a bearing clearance measuring device and by a rudder for a ship and a method for measuring the wear of a bearing.

In accordance with the invention, a bearing for supporting a shaft, in particular a rudder shaft, or a rudder blade is proposed, comprising a first bearing element and a second bearing element, wherein the first bearing element has a sliding surface for contacting the second bearing element in a sliding manner, and at least one measurand sensor having a wear surface for contacting the second bearing element in a sliding manner, wherein the at least one measurand sensor is not pin-shaped.

In the embodiment according to the invention of the bearing for supporting a shaft, the bearing can be formed for example as a bearing for a rudder shaft. However, the bearing for supporting a shaft can also be designed as a bearing for a propeller shaft, in particular for a propeller shaft of a watercraft. In addition, the bearing according to the invention is suitable in principle for any axis or bearing, in particular a highly loaded axis or bearing, in which case there may be axis play or bearing clearance or journal bearing clearance as a result of axis wear or bearing wear. In particular, the bearing according to the invention is suitable for any plain bearing in which wear and therefore an increase in the bearing clearance can occur, in particular under high load. The bearing can be designed as a plain bearing, for example as a journal bearing comprising a plain bearing. The bearing can also preferably be designed as a radial bearing, however, the invention is also suitable for an axial bearing or a combined radial and axial bearing. In the sense of the invention, the bearing can thus be designed as a plain bearing, journal bearing, radial bearing, axial bearing, combined radial and axial bearing, and combinations of the specified bearing types and also any other suitable bearing.

If the bearing according to the invention is designed to support a rudder shaft, the bearing can thus be arranged in a lower end region of a rudder shaft, for example between a lower end region of the rudder shaft and a rudder trunk. In addition, however, it is also possible for the bearing according to the invention to be arranged in an upper end region of a rudder shaft, in particular in an upper end region of a rudder shaft arranged inside a ship's hull. One or more such bearings for supporting a shaft, in particular a rudder shaft, can be arranged on a shaft, in particular on a rudder shaft. The bearings can also be arranged at any suitable position of the rudder shaft. The first bearing element of the bearing is formed with a sliding surface for contacting the second bearing element in a sliding manner, wherein the second bearing element is preferably arranged on the shaft, in particular on the rudder shaft and/or on the propeller shaft, and the first bearing element is preferably arranged on a guide element, such as a rudder trunk or a housing for a propeller shaft. The measurand sensor according to the invention is also designed with a wear surface for contacting the second bearing element in a sliding manner. Due to the provision of a wear surface of the measurand sensor, it is advantageously possible for the wear of the wear surface of the measurand sensor to represent the wear of the bearing or to be related to the wear of the bearing. The wear of the measurand sensor can thus indicate a wear of the bearing for supporting a shaft. The wear of the wear surface of the measurand sensor occurs here in particular by the sliding of the wear surface against the second bearing element.

In the present case, a measurand sensor is also understood to mean a sensor or a probe or a measuring apparatus. In particular, the term measurand sensor comprises any device which can determine the wear of a wear surface of the measurand sensor and, optionally, can forward information or data regarding the wear.

A particular advantage results from the fact that the measurand sensor is not pin-shaped, wherein the term "pin-shaped measurand sensor" is understood to mean a measurand sensor which has a cylindrical body and a substantially elongate design. An elongate design is provided preferably when the ratio of the length of the longitudinal axis of the measurand sensor to the length or extent of the measurand sensor perpendicularly to the longitudinal axis is greater than 1.2, preferably greater than 1.5, particularly preferably greater than 2.0. The term "pin-shaped measurand sensor" can also include a measurand sensor which has a cross-section in the form of a polygon and a substantially elongate design. In particular, a pin-shaped measurand sensor is understood to mean a measurand sensor which has a cylindrical body or a cross-section in the form of a polygon and a substantially elongate design, wherein the wear surface is preferably substantially perpendicular or transverse to the longitudinal axis of the measurand sensor.

Although the new measurand sensor can have a body with a cross-section in the form of a polygon and a substantially elongate design, the wear surface is then not arranged on one of the end faces of the measurand sensor or is not arranged on one of the sides, outer sides or planes substantially perpendicular or transverse to the longitudinal axis of the measurand sensor. In this case the new measurand sensor is thus preferably not pin-shaped, in such a way that the wear surface is not perpendicular or transverse to the longitudinal axis of the measurand sensor. The wear surface of the measurand sensor is preferably substantially parallel to the longitudinal axis of the measurand sensor. In this case the wear surface is not arranged on an end face, but on a side face parallel to the longitudinal axis of the measurand sensor.

Cylindrical wear pins are known from the prior art which have a wear surface on one of the end faces of the cylindrical wear pin. The known wear pins are arranged in an outer bearing portion such that they pass through the latter and the longitudinal axis of the wear pin is perpendicular to the inner bearing portion. Due to the orientation and shaping of the known wear pin, said pin is vulnerable with respect to shear forces. There is thus a risk of damage to the wear pin as a result of friction and shearing forces occurring with sliding contact of the wear pin against an inner bearing portion.

If the new measurand sensor is not pin-shaped, wherein it can indeed have a substantially elongate design, although the wear surface is then not substantially perpendicular or transverse to the longitudinal axis of the measurand sensor, but instead is preferably oriented substantially parallel to the longitudinal axis of the measurand sensor, the measurand sensor can thus be brought via the wear surface into sliding contact with the second bearing element, in such a way that the longitudinal axis is not perpendicular to the second bearing element. The risk of damage to the measurand sensor as a result of friction and shearing forces occurring with sliding contact of the measurand sensor against the second bearing element is thus advantageously reduced.

Due to the omission of pin-shaped measurand sensors, the bearing for supporting a shaft, comprising the measurand sensor, can withstand high loads, which in particular occur in a bearing for supporting a rudder shaft. The non-pin-shaped measurand sensor is preferably fixedly connected to the first bearing element and in particular cannot be disassembled or removed from the first bearing element.

Advantageous developments of the invention are characterised in the dependent claims.

The wear surface of the measurand sensor is preferably designed in a manner corresponding to a portion of the lateral surface of a cylinder or cone.

A portion of the lateral surface of a cylinder or cone in the present case denotes any sub-area, and in particular also the entire area, of the lateral surface of a cylinder or cone. A portion of the lateral surface of a cylinder or cone is also understood to mean both a portion of the inner side of the lateral surface of a cylinder or cone and a portion of the outer side of the lateral surface of a cylinder or cone, such that, depending on the viewpoint, the portion of the lateral surface of a cylinder or cone has a convex shape, when viewing the portion of an outer surface of the lateral surface of a cylinder or cone, or has a concave shape, when viewing the portion of the inner surface of the lateral surface of a cylinder or cone. The advantage according to the invention results from the fact that, with a second bearing element having a sliding surface complementary to the shape of the wear surface of the measurand sensor, on which sliding surface the wear surface of the measurand sensor can be arranged in a sliding manner, there is always flush contact between the wear surface of the measurand sensor and the complementary sliding surface of the second bearing element. In particular it is therefore expedient for the sliding surface of the second bearing element, on which the wear surface of the measurand sensor can be arranged for sliding contact, to likewise have the shape of a portion of the lateral surface of a cylinder or cone, wherein the corresponding imaginary cylinder has substantially the same radius as the corresponding imaginary cylinder forming the basis of the shaping of the wear surface of the measurand sensor. Due to the design according to the invention of the wear surface of the measurand sensor and the resulting flush contact between the wear surface of the measurand sensor and the sliding surface of the second bearing element, a continuous detection or determination of the wear of the measurand sensor and therefore of the bearing for supporting a shaft is possible, since wear of the wear surface of the measurand sensor is representative for the wear of the bearing or is directly related to the wear of the bearing on account of the flush contact of the wear surface of the measurand sensor with the sliding surface of the second bearing element.

More preferably, a measurand sensor receptacle or a recess, in particular a preferably slot-shaped blind bore, or a groove or a channel or a step is arranged in the sliding surface of the first bearing element, wherein the at least one measurand sensor is arranged in the measurand sensor receptacle or the recess, and wherein the measurand sensor can be inserted into the measurand sensor receptacle and/or can be removed from the measurand sensor receptacle exclusively from the side of the sliding surface.

In particular with a design of the measurand sensor receptacle or of the recess in the form of a slot-shaped or elongate blind bore or groove or channel or step, which is preferably provided in the longitudinal direction of the first bearing element in the sliding surface thereof, a measurand sensor having a substantially elongate design and a wear surface not extending perpendicularly or transversely to the longitudinal axis of the measurand sensor can be arranged or is arranged in the measurand sensor receptacle or the recess such that the longitudinal axis of the measurand sensor is not perpendicular to the sliding surface, and in the case of a bearing bush is not radial to the bearing bush. The longitudinal direction or longitudinal axis of the measurand sensor is then preferably parallel to the longitudinal direction of the bearing element, or in the case of a bearing bush is oriented in the longitudinal direction of the bearing bush or substantially in the peripheral direction of the bearing bush. The risk of damage to the measurand sensor as a result of shearing and friction forces is thus reduced.

Due to the advantageous arrangement of the measurand sensor in the measurand sensor receptacle or the recess, in particular in a preferably slot-shaped blind bore or a groove or a channel or a step, the measurand sensor can be recessed in the bearing element, and therefore the wear surface of the measurand sensor is arranged in particular in line or always flush with the sliding surface of the first bearing element. In particular, the measurand sensor does not protrude from the sliding surface of the first bearing element. This means advantageously that, with flush and sliding contact of the first bearing element against the second bearing element, the wear surface of the measurand sensor at the same time also contacts the second bearing element in a flush manner. In addition, it is advantageous that further holders or mounting or fastening devices for the measurand sensor do not have to be provided as a result of the arrangement of the measurand sensor in a measurand sensor receptacle or a recess of the first bearing element, thus resulting in a simplified production of the bearing comprising the measurand sensor. A preferably slot-shaped blind bore or groove or channel or step is particularly advantageously suitable here for receiving a measurand sensor which preferably is not pin-shaped. In addition, the design of the measurand sensor receptacle or of the recess in the form of a slot-shaped or elongate blind bore or groove or channel or step means that the wear can be measured not only substantially at a certain point or in a heavily localised manner, but that the wear can also be measured over a certain extended region determined by the elongate design of the measurand sensor receptacle or the recess or the measurand sensor received in the recess. An increased precision of the wear measurement is thus ensured.

Since the measurand sensor advantageously can be inserted into the measurand sensor receptacle and/or can be removed from the measurand sensor receptacle exclusively from the side of the sliding surface, the problem from the prior art that the wear pin arranged in the through-hole can have play in the through-hole, in particular radial play, is remedied. The measurand sensor is inserted here into the measurand sensor receptacle preferably from the side of the sliding surface, through the sliding surface, and is then supported, in particular in the radial direction, by a bottom or base of the measurand sensor receptacle or recess preferably provided in the measurand sensor receptacle or the recess, such that a radial play of the measurand sensor in the bearing element is avoided in a simple manner. In particular when the measurand sensor receptacle or the recess is formed as a blind bore, groove, channel or step, the blind bore, the groove, the channel or the step has a bottom or a base which, as considered from the direction of the sliding surface, preferably defines the lowest point of the blind bore, the groove, the channel, or the step. The base or the bottom then forms a contact face, in particular a radial contact face, for the measurand sensor, such that this is blocked against movement in the radial direction, in particular with a bearing bush.

The measurand sensor receptacle or the recess can preferably be arranged in the sliding surface of the first bearing element in the longitudinal direction or in the transverse or peripheral direction, such that the measurand sensor is then also preferably arranged in the sliding surface of the first bearing element in the longitudinal direction or in the transverse or peripheral direction. If the first bearing element is formed as part of a bearing for supporting a rudder shaft, in particular as a bearing bush, the longitudinal direction of the bearing element thus corresponds to the longitudinal direction of the rudder shaft when the latter is arranged in the bearing for supporting a rudder shaft. The measurand sensor receptacle or the recess, however, can also be provided in the sliding surface of the first bearing element in any other suitable orientation.

By arranging the measurand sensor or the measurand sensor receptacle or the recess in the longitudinal direction of the bearing element, a simplified production of the measurand sensor is possible, since the wear surface of the measurand sensor does not have to be adapted or only has to be marginally adapted to the curvature of the sliding surface, in particular when the first bearing element is formed as a bearing bush. Furthermore, any wear of the bearing or of the bearing element can also advantageously be determined over a larger measurement region in the longitudinal direction of the bearing element without the need for any additional measurand sensors.

In a preferred embodiment of the bearing for supporting a shaft, provision is made such that the first bearing element is a bearing bush, and/or that the first bearing element can be arranged on the inner side, in particular the inner wall, of a trunk pipe of a rudder trunk, and/or that the first bearing element can be arranged on the outer side of the trunk pipe of the rudder trunk, and/or that the second bearing element can be arranged on a rudder shaft or can be formed as part of a rudder shaft, and/or that the second bearing element can be arranged on a rudder blade, and/or that the bearing can be arranged between the trunk pipe and the rudder shaft, and/or that the bearing can be arranged between the trunk pipe and the rudder blade.

In an advantageous embodiment the first bearing element can thus be arranged on the inner side of a trunk pipe of a rudder trunk, and the second bearing element can be arranged on a rudder shaft or can be formed as part of a rudder shaft. In this advantageous embodiment the first and the second bearing element thus form a journal bearing or a radial bearing which supports a rudder shaft inside a rudder trunk or inside a trunk pipe of a rudder trunk. What is advantageously attained hereby is the supporting of a rudder shaft, preferably in the lower end region of the rudder shaft, in a rudder trunk at a position along the rudder shaft at which the greatest shear, torsional and compressive forces and stresses act on the rudder shaft, the trunk pipe of the rudder trunk, and the bearing. As a result of the advantageous arrangement, a wear of the bearing can thus be determined where the highest loads and therefore the greatest risk of wear of a bearing are present.

Furthermore, provision can advantageously be made such that the second bearing element is formed as part of a rudder shaft. In this advantageous embodiment it is therefore unnecessary to arrange an independent second bearing element on the rudder shaft, and instead the rudder shaft or a portion of the surface of the rudder shaft forms the second bearing element. Omitting the second bearing element or forming the second bearing element as part of the rudder shaft results in a simplified construction as well as lower maintenance and production costs.

It can also be advantageous that the first bearing element can be arranged on the outer side of the trunk pipe of the rudder trunk and that the second bearing element is arranged on a rudder blade, in particular on the inner side of a receiving cavity in the rudder blade for the rudder trunk. This advantageous embodiment is suitable in particular when the rudder blade is supported by a bearing arranged between the rudder blade and the trunk pipe of the rudder trunk.

In the case of this advantageous embodiment as well, it is possible in principle that the first bearing element is formed as part of the trunk pipe of the rudder trunk or that the second bearing element is formed as part of the rudder blade.

In addition, it is also possible in principle that the rolls of the first bearing element and of the second bearing element are swapped, so that for example the first bearing element can be arranged on a rudder shaft or can be formed as part of a rudder shaft or that the first bearing element can be arranged on a rudder blade.

Furthermore, it is also possible that the measurand sensor has a wear surface for contacting the first bearing element in a sliding manner, however, a measurand sensor having a wear surface for contacting the second bearing element in a sliding manner is preferred.

An expedient development of the bearing makes provision such that the measurand sensor has an electrically conductive material, that the electrically conductive material is arranged in the region of the wear surface of the measurand sensor for measuring the wear of the measurand sensor, and that the electrically conductive material is preferably formed as at least one layer or conductor layer and/or at least one conductor circuit and/or at least one conductor path.

An advantage of this embodiment is that a wear of the wear surface of the measurand sensor, and therefore a possible wear of the bearing for supporting a shaft, can be determined by continuously measuring the electrical conductivity or the resistance or a short circuit of the electrically conductive material. An automated and fault-resistant detection, determination, or monitoring of the wear of a journal bearing is thus advantageously possible.

The wear of the bearing is preferably measured by means of an electronic measurand sensor, which works completely without any moving components. It is also preferred that the measurement of the wear of the bearing can be carried out in the dry state and in the wet state of the bearing. If the bearing is designed as a bearing for a rudder shaft or for a propeller shaft, the measurement of the wear of the bearing can also be carried out in the immersed state of the bearing.

In the immersed state, the wear surface of the measurand sensor is generally surrounded by water, in particular seawater.

A further expedient embodiment makes provision such that the electrically conductive material is designed as at least two layers or conductor layers and/or as a least two conductor circuits and/or as a least two conductor paths, wherein, in an unworn state of the measurand sensor, the at least two layers or conductor layers and/or the at least two conductor circuits and/or the at least two conductor paths are electrically insulated from one another.

In an unworn state of the measurand sensor, there is thus no electrically conductive connection between the at least two conductor paths and/or conductor circuits and/or conductor layers, and therefore the electrical conductivity between the at least two layers or between the at least two conductor circuits and/or the at least two conductor paths substantially disappears or the electrical resistance between the two layers is fundamentally very high. In particular, no short circuit between the at least two layers, conductor circuits or conductor paths can be measured in the unworn state. If, advantageously, there is no short circuit or a substantially disappearing electrical conductivity measured between two conductor paths, layers or conductor circuits of the measurand sensor, the absence of the short circuit or the disappearance or the immeasurability of the electrical conductivity between the at least two layers, conductor circuits or conductor paths thus indicates an unworn measurand sensor and therefore indicates an unworn or only marginally worn bearing for supporting a shaft. If, by contrast, the wear surface of the measurand sensor has become worn and therefore the bearing for supporting a shaft has become worn, a short circuit can occur in the worn state between the at least two layers, conductor circuits or conductor paths, which short circuit can be measured and indicates wear of the bearing or indicates journal bearing clearance. The measurement of the electrical resistance or of a short circuit thus constitutes a particularly simple embodiment of the measurement of the wear of a bearing for supporting a shaft.

Preferably, 2 to 20 layers or conductor layers and/or conductor circuits and/or conductor paths are provided. Particularly preferably, 3 to 10 layers or conductor layers and/or conductor circuits and/or conductor paths are provided.

There are thus preferably two measurement methods available for measuring wear of the wear surface of the measurand sensor. In a first measurement method the wear of the wear surface can be determined in that one or more layers or conductor layers and/or conductor circuits and/or conductor paths are worn or destroyed, i.e. these layers, conductor circuits or conductor paths are no longer electrically conductive. A sudden rise of the electrical resistance of an individual layer or of a number of layers, conductor circuits or conductor paths thus indicates the degree of wear of the wear surface of the measurand sensor. This measurement method is suitable for dry bearings. A dry bearing can be present, for example in the case of a bearing for a rudder shaft, when the ship is in a dry dock or sails without ballast, such that the bearing is above the water surface.

In a second measurement method an electrical conductivity or a short circuit between at least two layers, conductor circuits or conductor paths is measured. This is therefore advantageous in particular since the second measurement method can be applied also in the case of a wet bearing or in the case of an electrically conductive second bearing element, such as a metal rudder shaft. If, specifically, the bearing is in an immersed and therefore wet state, the bearing is thus flooded with water or seawater. If an individual layer, conductor circuit or conductor path is worn, the seawater can continue to produce the electrical contact between the ends or end faces of the remains or connections of the individual layer, the individual conductor circuit, or the individual conductor path. If, by contrast, a metal shaft such as a metal rudder shaft rests against the wear surface of the measurand sensor, the electrical contact in the case of a worn layer, conductor circuit or conductor path can thus be produced between the ends or the end faces of the remains or connections of the individual layer, the individual conductor circuit, or the individual conductor path by the metal shaft.

By contrast, in the second measurement method a short circuit can occur between various layers, conductor circuits or conductor paths only in a worn state, since in the unworn state the individual conductor layers, conductor circuits or conductor paths are electrically insulated from one another.

The preferred embodiment thus offers two complementary measurement methods for measuring the wear of the wear surface of a measurand sensor, wherein in particular the second measurement method for measuring a short circuit between two conductor layers, conductor circuits or conductor paths in the case of a wet bearing is to be preferred. However, both measurement methods can also be applied at the same time.

In an unworn state of the measurand sensor, the at least two layers or conductor layers and/or the at least two conductor circuits and/or the least two conductor paths are preferably insulated from one another and with respect to the surrounding environment in a watertight manner.

A particularly advantageous development makes provision such that the at least two layers or conductor layers and/or conductor circuits and/or conductor paths are arranged at a different distance from the wear surface, and/or that the at least two layers or conductor layers and/or conductor circuits and/or conductor paths are arranged adjacently from one another, preferably at a distance of from 100 µm to 1000 µm, particularly preferably at a distance of from 200 µm to 700 µm, in particular preferably at a distance of from 400 µm to 600 µm.

Here, the respective distances between the at least two layers, conductor circuits or conductor paths and the wear surface can preferably be constant at least in a region in the vicinity of the wear surface or at any point of the conductor circuits, conductor paths or layers, wherein the distances are determined for example from the points of intersection of an orthogonal of the wear surface with the layers, conductor circuits or conductor paths, however, these distances can also vary along a conductor layer, a conductor circuit or a conductor path. The difference in the distances of the conductor layers, or conductor circuits or conductor paths can also be constant or can vary, wherein the difference in the distances is determined for example from the points of intersection of an orthogonal of the wear surface with the layers, conductor circuits or conductor paths. However, it is also possible in principle for the layers, conductor circuits or conductor paths to have the same distance from the wear surface of the measurand sensor. The layers, conductor circuits or conductor paths are particularly preferably oriented or arranged substantially parallel to the wear surface and/or parallel to one another at least in a region in the vicinity of the wear surface. It is also preferred for the layers, conductor circuits or conductor paths to lie side by side, i.e. to lie at least in part in a common imaginary surface or plane, wherein the surface or plane is preferably oriented parallel to the wear surface. Since the wear surface is formed in a manner corresponding to a portion of the lateral surface of a cylinder, the surface or plane is preferably likewise formed as a portion of the lateral surface of a cylinder. However, the surface or plane can also be un-curved. Further layers, conductor circuits or conductor paths can then also lie at least in part in a further surface or plane, wherein the further surface or plane is preferably oriented parallel to the wear surface, but has a different distance from the wear surface compared with the first surface or plane.

Furthermore, it is in particular also possible that the layers, conductor paths or conductor circuits protrude from the wear surface or end directly at the wear surface. The layers, conductor paths or conductor circuits can also be arranged at an angle, preferably at a right angle, to the wear surface or can taper theretoward. The layers, conductor paths or conductor circuits can then protrude from the wear surface or can end in the wear surface or can end in the vicinity of the wear surface, i.e. in a region of the measurand sensor, which is arranged in the vicinity of the wear surface, preferably in the direct vicinity thereof.

This results in an advantage in particular when the at least two layers, conductor circuits or conductor paths are arranged at different distances from the wear surface, wherein the distances are additionally substantially preferably constant. If the wear surface becomes worn, the wear surface is abraded layer by layer until ultimately the first conductor layer, conductor circuit or conductor path is exposed and is in direct, sliding contact with the second bearing element. If further abrasion now takes place, the first layer or conductor circuit or conductor path is destroyed, which, in particular in the case of a dry bearing, leads to a sudden measurable rise in the electrical resistance of the first conductor layer, whereby wear of the wear surface can be determined. If abrasion then continues to take place, the second or the further layers, conductor circuits or conductor paths ultimately also become exposed on the wear surface and can likewise be destroyed as a result of further wear, whereby continued wear can now be determined. In addition, it is also possible that, with wear of the wear surface of the measurand sensor, the position and shape of the layers, conductor circuits or conductor paths is modified, in particular by shear forces, compressive forces or tension forces, such that these come into electrical contact with one another in the worn state and a short circuit thus occurs between the layers, conductor circuits or conductor paths. This is the case in particular when the layers, conductor paths or conductor circuits are arranged at an angle, preferably at a right angle, to the wear surface or taper theretoward.

It is preferred, however, that the at least two layers or conductor layers and/or conductor circuits and/or conductor paths are arranged substantially parallel to the wear surface. In this case, successively further layers, conductor circuits or conductor paths are exposed on the wear surface as result of abrasion and can also be destroyed by further wear. A short circuit is produced between various layers, conductor circuits or conductor paths by water, in particular seawater, or by a metallic second bearing element. If an electrical short circuit of this type takes place, the wear of the measurand sensor and therefore of the bearing can be determined by the determination of this short circuit. The further the abrasion of the wear surface of the measurand sensor has progressed, the greater is the number of layers, conductor circuits or conductor paths disposed close to the wear surface, since the distance of the layers, conductor paths or conductor circuits from the wear surface has decreased. Wear of the wear surface of the measurand sensor, and in particular the extent of the wear of the wear surface of the measurand sensor, can thus be determined by successive determination of short circuits between various conductor paths, layers or conductor circuits, in particular between adjacent conductor paths, layers or conductor circuits or by successive determination of changing electrical resistances of the conductor paths, layers or conductor circuits. In order to precisely determine the wear, it is expedient that the layers, conductor circuits or conductor paths are arranged only at a short distance from one another or from the wear surface. This distance preferably lies in a range of from 100 µm to 1000 µm, particularly preferably in a range of from 200 µm to 700 µm, in particular preferably in a range of from 400 µm to 600 µm. The distance determines the measurement accuracy. If even a number of conductor layers, conductor circuits or conductor paths are arranged at least in part in a surface or plane parallel to the wear surface, a short circuit can thus be measured between these conductor layers, conductor circuits or conductor paths. In this case, for the measurement of wear, the abrasion does not have to be continued to such an extent that already a number of conductor layers, conductor circuits or conductor paths arranged at a different distance from the wear surface are destroyed.

A further expedient development of the subject matter of the invention is characterised in that the measurand sensor comprises a control unit, wherein the control unit is designed to detect wear of the measurand sensor by measuring the change of the electrical resistance and/or by measuring a short circuit between two layers and/or conductor circuits and/or conductor paths that are electrically insulated from one another in the unworn state of the measurand sensor.

The provision of a control unit has the advantage that the measurement of the change in resistance and/or the measurement of a short circuit can be automated, which leads to an advantageous simplification and immunity to faults of the measurement process. Furthermore, the control unit can comprise, for example, a computing unit, in particular a programmable computing device, such as a microprocessor. As a result of appropriate programming, the operating principle of the control unit or of the measurand sensor can thus be defined advantageously. By way of example, it is possible to determine that the control unit perpetually or continuously measures the electrical resistance or a short circuit between two layers, conductor circuits or conductor paths of the measurand sensor. However, the measurement can also take place at previously defined intervals. Measurement ranges and measurement tolerances for the change of the electrical resistance or for the measurement of a short circuit can also be defined. It is also possible in principle that the control units of the measurand sensors continuously or at predefined time intervals send a measured change of an electrical resistance or of a short circuit to a superordinate computing unit. The information from a number of measurand sensors can then be combined in the superordinate computing unit, such that a precise measurement of the wear or of the bearing clearance or journal bearing clearance of the bearing can be determined, in particular in the case of measurand sensors distributed over the periphery of a rudder shaft or a bearing. The control units of the measurand sensors more advantageously can also have a power supply, such as a battery. However, provision is preferably made such that the measurand sensors or the control units of the measurand sensors are supplied with power via an external electrical power source. The electrical power source supplies the measurand sensor with electrical voltages preferably of between 2 V and 10 V, particularly preferably of 5 V. The power supply is more preferably galvanically isolated for example from an on-board power supply of a ship.

However, the control units can also be arranged outside the measurand sensor. However, the control unit or the superordinate computing unit must in any case be operatively connected for the measurement of an electrical resistance or a short circuit, wherein the operative connection is preferably produced by electrically conductive conduction means. Furthermore, it is also possible that no control units are provided and that the superordinate computing unit carries out the logical querying of the layers, conductor circuits or conductor paths with regard to the measurement of an electrical resistance or a short circuit.

In a particular embodiment of the bearing, provision is made such that the electrically conductive material is arranged in a carrier, in particular a circuit board or a printed circuit board, and/or that the electrically conductive material and/or the carrier is arranged or moulded in a non-metal material, in particular in a synthetic resin.

The advantageous arrangement of the electrically conductive material in a carrier or a circuit board or a printed circuit board ensures a stationary fixing of the electrically conductive material in the unworn state, which is changed only by increasing wear of the wear surface of the measurand sensor, and therefore also of the carrier, in particular of the circuit board or the printed circuit board. This enables a precise and reliable determination of a wear of the wear surface of the measurand sensor. The arrangement of the electrically conductive material in the carrier, in particular in a circuit board or a printed circuit board, advantageously also allows that the control unit of the measurand sensor can likewise be arranged on or in the carrier, such that an easily preproducible measuring unit of the measurand sensor, consisting of carrier or circuit board or printed circuit board, electrically conductive material and control unit is provided. This results in cost-efficient production. In addition, the production of the bearing is simplified, since only the overall unit, consisting of carrier and electrically conductive material and optionally the control unit, has to be arranged in the bearing.

By moulding the electrically conductive material in a non-metal material, in particular in a synthetic resin, a measurand sensor which is adapted to the spatial conditions of the bearing can be provided on account of the plasticity of the synthetic resin or of a non-metal material during the moulding process. This in particular opens up a variety of possible applications of the bearing or of the measurand sensor of the bearing. Here, the electrically conductive material can also be moulded directly in the non-metal material or in the synthetic resin, however, it is also possible for the carrier, in particular the circuit board or the printed circuit board, comprising the electrically conductive material to be moulded in the synthetic resin.

A further preferred embodiment makes provision such that the first bearing element and/or the second bearing element has a measurand sensor receptacle or a recess, in particular a preferably slot-shaped blind bore or a groove or a channel or a step, and that the at least one measurand sensor is arranged in the measurand sensor receptacle or the recess, wherein the measurand sensor is preferably fixed in the measurand sensor receptacle or the recess using a non-metal material, in particular using a synthetic resin.

Due to the advantageous arrangement of the measurand sensor in the recess, it is made possible for the measurand sensor to be recessed in the bearing element so that the wear surface of the measurand sensor is arranged in particular in line or always flush with the sliding surface of the first bearing element. In particular, the measurand sensor does not protrude from the sliding surface of the first bearing element. This advantageously means that, when the first bearing element contacts the second bearing element in a flush and sliding manner, the wear surface of the measurand sensor also at the same time contacts the second bearing element in a flush manner.

In addition, it is advantageous that, by arranging the measurand sensor in a recess of the first bearing element, further holders or mounting or fastening devices for the measurand sensor do not have to be provided, thus resulting in a simplified production of the bearing comprising the measurand sensor. A preferably slot-shaped blind bore or groove or channel or step is particularly advantageously suitable here for receiving a measurand sensor which preferably is not pin-shaped. In addition, the design of the recess in the form of a slot-shaped or elongate blind bore or groove or channel or step means that the wear can be measured not only substantially at a certain point or in a heavily localised manner, but that the wear can also be measured over a certain extended region determined by the elongate design of the recess or the measurand sensor received in the recess. An increased precision of the wear measurement is thus ensured. The fixing of the measurand sensor with a non-metal material, in particular with a synthetic resin, ensures a secure fixing of the measurand sensor within the recess so that this cannot fall out of the recess, not even when the shaft is removed, for example when the rudder shaft is removed. In addition, the non-metal material or the synthetic resin has an abrasion resistance that is lower than that of the first bearing element and/or the second bearing element. It is thus advantageously ensured that the wear surface of the measurand sensor is always in line with the sliding surface of the first and/or second bearing element and that the wear of the wear surface of the measurand sensor measured by the measurand sensor correctly represents the wear of the bearing or of the bearing elements. However, it is also possible in principle that the abrasion resistance of the synthetic resin or the abrasion resistance of the measurand sensor is equal to, greater than, or smaller than the abrasion resistance of the first and/or the second bearing element.

A further preferred development of the bearing is characterised in that an opening passing through the bearing element, in particular a through-hole, is formed in a wall and/or side wall of the measurand sensor receptacle or the recess, preferably in the bottom and/or the base of the measurand sensor receptacle or the recess, and in that a signal conduction means, in particular an electrical line or a cable, of the measurand sensor is guided through the opening.

The opening passing through the bearing element preferably has a diameter between 0.5 mm and 5 cm, particularly preferably between 1 mm and 2 cm, in particular preferably between 5 mm and 1 cm.

The recess or the measurand sensor receptacle thus has a diameter larger than the opening or the through-hole. The recess or the measurand sensor receptacle can also taper in the direction of the opening so that the diameter of the recess or of the measurand sensor receptacle in the plane of the sliding surface of the first bearing element is larger than the diameter of the opening or through-hole. It is thus ensured that the recess or the measurand sensor receptacle has a bottom or a base which can serve as a contact face for the measurand sensor in order to prevent any play, in particular radial play, of the measurand sensor in the recess. In the case of a tapering recess or a tapering measurand sensor receptacle, the side walls of the recess or of the measurand sensor receptacle converging toward one another act as contact faces.

The recess or the measurand sensor receptacle preferably has a depth corresponding to between 10% and 90% of the thickness of the bearing element, in particular of the first bearing element. The recess or the measurand sensor receptacle particularly preferably has a depth corresponding to between 20% and 70% of the thickness of the bearing element. The recess or the measurand sensor receptacle in particular preferably has a depth corresponding to between 30% and 50% of the thickness of the bearing element.

The signal conduction means is preferably connected to the measurand sensor or to the control unit of the measurand sensor and is designed to forward the measurands recorded by the measurand sensor, in particular the measurands relating to the wear of the measurand sensor. The signal conduction means preferably forwards the measurands of the measurand sensor to a superordinate computing unit, which preferably receives data from a plurality of measurand sensors. The signal conduction means is expediently an electrical line or a cable through which electrical signals can be conducted in analogue or digital form, which the control unit preferably sends to a superordinate computing unit. However, it is also possible in principle that the signal conduction means is connected directly to the electrically conductive material, or the layers or conductor circuits or conductor paths, and that the superordinate computing unit or controller directly measures the electrical resistance or a short circuit of the electrically conductor layers, conductor circuits or conductor paths, without intermediate control units of the measurand sensors. The signal conduction means can also be connected to a transmitting and/or receiving unit, which sends the data obtained from the control unit wirelessly to a superordinate computing unit, or receives data and instructions from a superordinate computing unit and forwards these to the control unit of the measurand sensor. A means for supplying power to the measurand sensor or the control unit of the measurand sensor, in particular an electrically conductive cable or a wire, can also be guided through the opening. Preferably, merely the signal conduction means and optionally the means for power supply is/are guided through the opening in a sidewall of the recess. In particular, no pin-shaped measurand sensor is guided through the opening.

In a particularly expedient embodiment of the invention provision is made such that the first bearing element is embodied as a bearing bush, that the bearing has a segmented ring, wherein at least one of the segments of the segmented ring comprises the at least one measurand sensor, and the segmented ring is preferably arranged in a recess running around in the peripheral direction on the inner side of the bearing bush.

The segmented ring preferably has an inner side or inner face. The at least one segment of the segmented ring comprising the at least one measurand sensor likewise has an inner side or an inner face. The inner side or the inner face of the segment of the segmented ring comprising the at least one measurand sensor is formed here at least in part as a wear surface of the measurand sensor. The segment comprising the at least one measurand sensor is also referred to as a sensor segment. By providing the segmented ring and forming at least one of the segments of the segmented ring as a sensor segment, the measurand sensor or the bearing can be handled in a particularly simple manner. The segments of the segmented ring which do not comprise a measurand sensor are also referred to as clamping segments. Clamping segments and sensor segments preferably alternate over the periphery of the segmented ring. Here, the sensor segments and the clamping segments can be arranged fixed to one another, however, it is also possible that the segments are inserted individually into the recess running around on the inner side of the bearing bush in the peripheral direction or are arranged in the recess. It is also expedient that both sensor segments and clamping segments have a similar, in particular the same abrasion resistance, and therefore the segmented ring has a similar or identical abrasion behaviour over the entire inner side or inner face of the segmented ring and has an approximately similar or identical material removal under load. The sensor segments and/or the clamping segments can comprise or consist of bronze. However, the sensor segments and/or the clamping segments can also comprise or consist of other suitable materials, for example synthetic material or synthetic resin.

In a further expedient embodiment of the bearing, provision is made such that the bearing bush is formed in two parts, wherein a first bearing part and a second bearing part are preferably formed as sub-bearing bushes with a reduced axial length compared with the bearing bush, wherein the segmented ring is arranged between the first bearing part and the second bearing part, wherein the bearing parts, at their regions facing toward one another, preferably have a preferably L-shaped profile running around in the peripheral direction, wherein the adjacently arranged, preferably L-shaped profiles form a recess, in which the segmented ring is arranged.

Due to the preferred arrangement of the segmented ring in the recess, the segmented ring is axially secured in the bush assembly formed of first bearing part and second bearing part. Here, the L-shaped profile can be provided preferably by forming a step or a channel. A particularly simple construction of the bearing is made possible with this advantageous embodiment. The first bearing part can preferably be provided. The segmented ring is then particularly preferably arranged in the L-shaped profile running around the first bearing part in the peripheral direction and is connected to the first bearing part in a watertight manner. The second bearing part is then arranged on the first bearing part in such a way that the L-shaped profile running around the second bearing part in the peripheral direction is likewise arranged on the segmented ring. The second bearing part is then also connected in a watertight manner to the peripheral ring and the first sub-bearing. Once these steps have been carried out, a continuous, one-part bearing bush is thus obtainable, which comprises a segmented ring, wherein at least one of the segments comprises at least one measurand sensor. The bearing bush, consisting of first bearing part, second bearing part and segmented ring, can then be arranged for example in a trunk pipe of a rudder trunk. In order to ensure a secure fit of the bearing bush in the trunk pipe of the rudder trunk, the bearing bush can be frozen for the insertion of the bearing bush into the trunk pipe. However, it is also possible that initially only the first bearing part is frozen and inserted into the trunk pipe. The segmented ring is then inserted into the trunk pipe such that the segmented ring is received in the L-shaped profile running around the first bearing part in the peripheral direction. The segmented ring can also be frozen for this purpose. Lastly, the second bearing part is frozen and inserted into the trunk pipe such that the L-shaped profile running around the second bearing part is arranged on the segmented ring. After each of these individual steps or once all of these individual steps have been performed, the individual elements, i.e. the first bearing part and second bearing part and also the segmented ring, are connected to one another in a watertight manner.

A particular advantage of the two-part embodiment of the bearing bush is that, after arrangement of the segmented ring in the recess running around the inner side of the bearing bush, the segmented ring comprising the at least one measurand sensor is disposed in a particularly favourable measurement position within the first bearing element or the bearing bush.

Alternatively or additionally, however, it would also be possible to attach a segmented ring comprising at least one segment having a measurand sensor to the end face of the bearing bush. However, the attachment of the segmented ring within the bearing bush is advantageous, since generally the wear at the end faces of the bearing bush often is not as severe as in the bearing itself.

In a further aspect, the object forming the basis of the invention is achieved by a bearing clearance measuring device, in particular for measuring the bearing clearance of a bearing, in particular a journal bearing, of a rudder shaft or a rudder blade, comprising a bearing according to any one of the previously described embodiments, wherein provision is made such that the bearing clearance measuring device has a computing unit which is designed to receive and to process signals and/or information of the at least one measurand sensor.

The bearing clearance measuring device can also be referred to as a wear measuring device or as a bearing-wear measuring device.

The computing unit of the bearing clearance measuring device is advantageously designed to receive and process signals and/or information from at least two measurand sensors. The computing unit is preferably designed in such a way that, if increased wear is detected, a warning or a signal or a message is output. The message can be output on an output unit and can comprise a visual or acoustic message. The computing unit can also have a memory unit so that the abrasive wear of the bearing for supporting a shaft can be documented without gaps or continuously by storing and evaluating the data of the at least one measurand sensor. A further expedient development makes provision such that the computing unit of the bearing clearance measuring device sends signals and information to at least one measurand sensor. The computing unit can thus prompt a measurand sensor, for example by sending a signal to said measurand sensor, to determine the current wear of the bearing clearance measuring device by measuring an electrical resistance and/or a short circuit.

If wear of the bearing clearance measuring device or of the bearing for supporting a shaft is indicated on the output device, appropriate steps can be taken, for example a replacement of the bearing for supporting a shaft.

In a further aspect, the object forming the basis of the invention is achieved by providing a rudder for a ship, comprising a rudder shaft and a rudder blade arranged on the rudder shaft, wherein provision is made such that the rudder comprises a bearing in one of the previously described embodiments and/or a previously described bearing clearance measuring device.

In an advantageous development of the rudder, provision is made such that the rudder has a rudder trunk comprising a trunk pipe, the bearing is arranged between the trunk pipe and the rudder shaft, and/or the bearing is arranged between the trunk pipe and the rudder blade, and/or the trunk pipe on the outer side or inner side has a guide means, in particular a recess, a groove or a cable channel, and a signal conduction means, in particular an electrical line or a cable, of the measurand sensor is arranged in the guide means in such a way that signals and/or information and/or electrical power can be conducted or transferred between the measurand sensor and a computing unit.

Due to the advantageous arrangement of the signal conduction means in the guide means, for example in a channel arranged on the trunk pipe on the inner side or outer side, the signal conduction means is prevented from being damaged. In particular, by laying the signal conduction means in the guide means, it is ensured that this signal conduction means, in particular the cable or electrical lines, is not damaged as the rudder shaft is inserted or as the rudder shaft rotates and/or as the rudder trunk is inserted into the ship's hull.

In accordance with a further advantageous embodiment, the rudder is characterised in that a spacer formed preferably as a clamping ring is provided, and in that the spacer preferably can be attached to the inner side of the trunk pipe in such a way that damage to the measurand sensor during the insertion of the rudder shaft into the trunk pipe of the rudder trunk can be avoided.

In a further aspect of the invention it is proposed that, in a method for measuring a bearing clearance and/or wear of a bearing for a shaft, in particular for a rudder shaft, or for a rudder blade, which method can be carried out with a bearing according to any one of the previously described embodiments, with a previously described bearing clearance measuring device, or with a rudder according to any one of the previously described embodiments, at least one measurand sensor which is not pin-shaped and which has at least two layers and/or conductor circuits and/or conductor paths made of an electrically conductive material is arranged in a bearing for supporting a shaft, in particular a rudder shaft, or a rudder blade, that the electrical resistance of the at least two layers and/or conductor circuits and/or conductor paths is measured, and that a bearing clearance and/or wear of the bearing is determined when a change of the electrical resistance of at least one of the two layers and/or conductor circuits and/or conductor paths is measured, and/or a bearing clearance and/or wear is determined when a short circuit is measured between two of the layers and/or conductor circuits and/or conductor paths.

The method is suitable both for determining a bearing clearance and wear of the bearing. In particular when bearing clearance is caused by wear of the bearing, bearing clearance is determined by measuring a wear of the bearing.

In an advantageous embodiment of the method it is proposed that measured values and/or jumps in the measured value of the electrical resistance and/or a short circuit are stored, and/or that at least one layer and/or a conductor circuit and/or a conductor path made of an electrically conductive material is severed, preferably by grinding down the wear surface of the measurand sensor before the measurand sensor is arranged in the bearing, and that a reference measurement and/or test measurement of the electrical resistance and/or a short circuit is taken.

By storing the jumps in the measured value or measured values of the electrical resistance of the short circuit, a gap-free documentation of the development of the bearing clearance and/or the course of the wear of the bearing for supporting a shaft, in particular a rudder shaft, can particularly advantageously be provided. By grinding down the wear surface of the measurand sensor, the advantage is also provided that false refluxes can occur with a change between water-lubricated and dry bearing conditions.

BRIEF DESCRIPTIONS OF THE DRAWINGS

Figure 2:
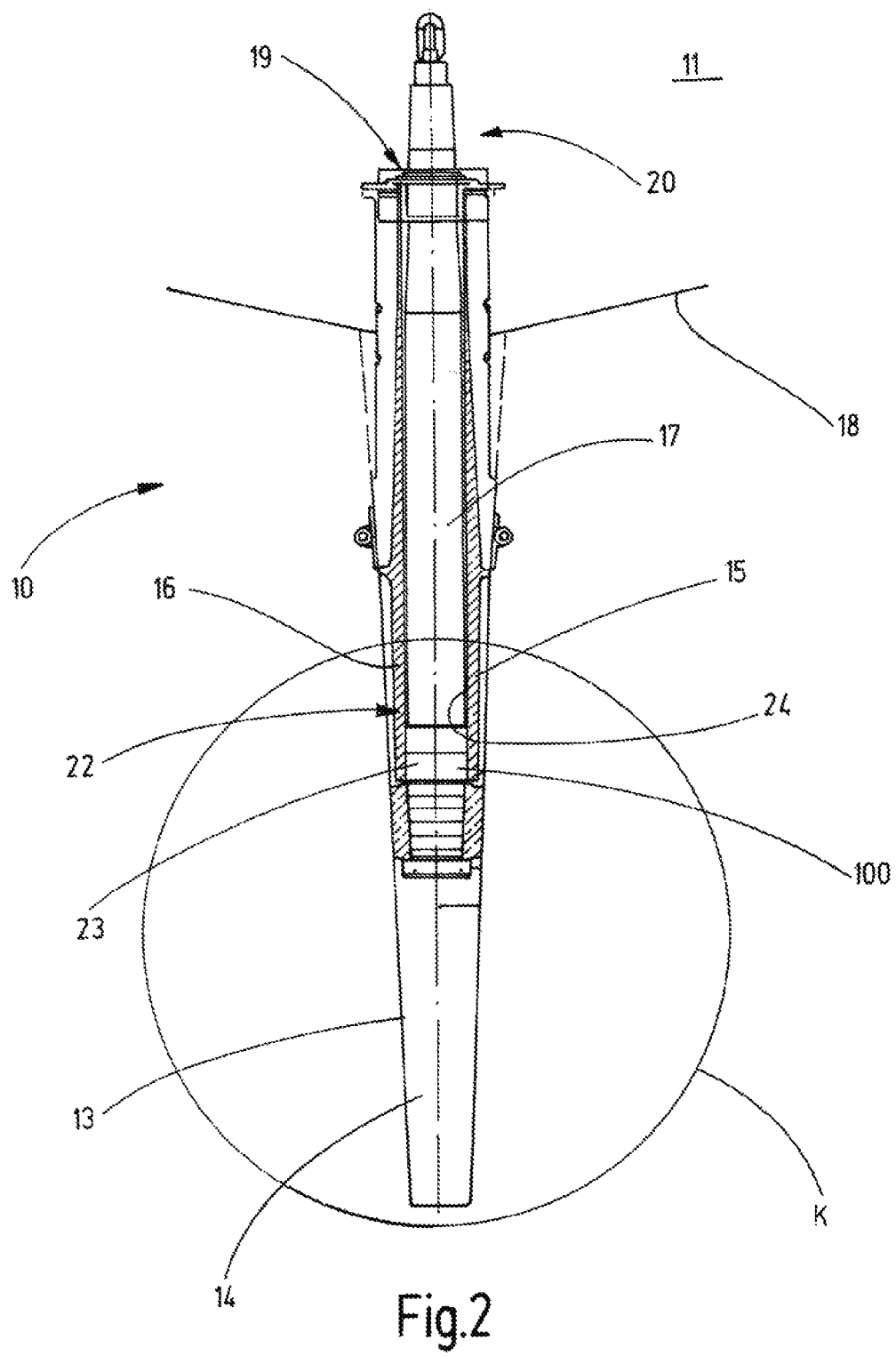
Figure 3:
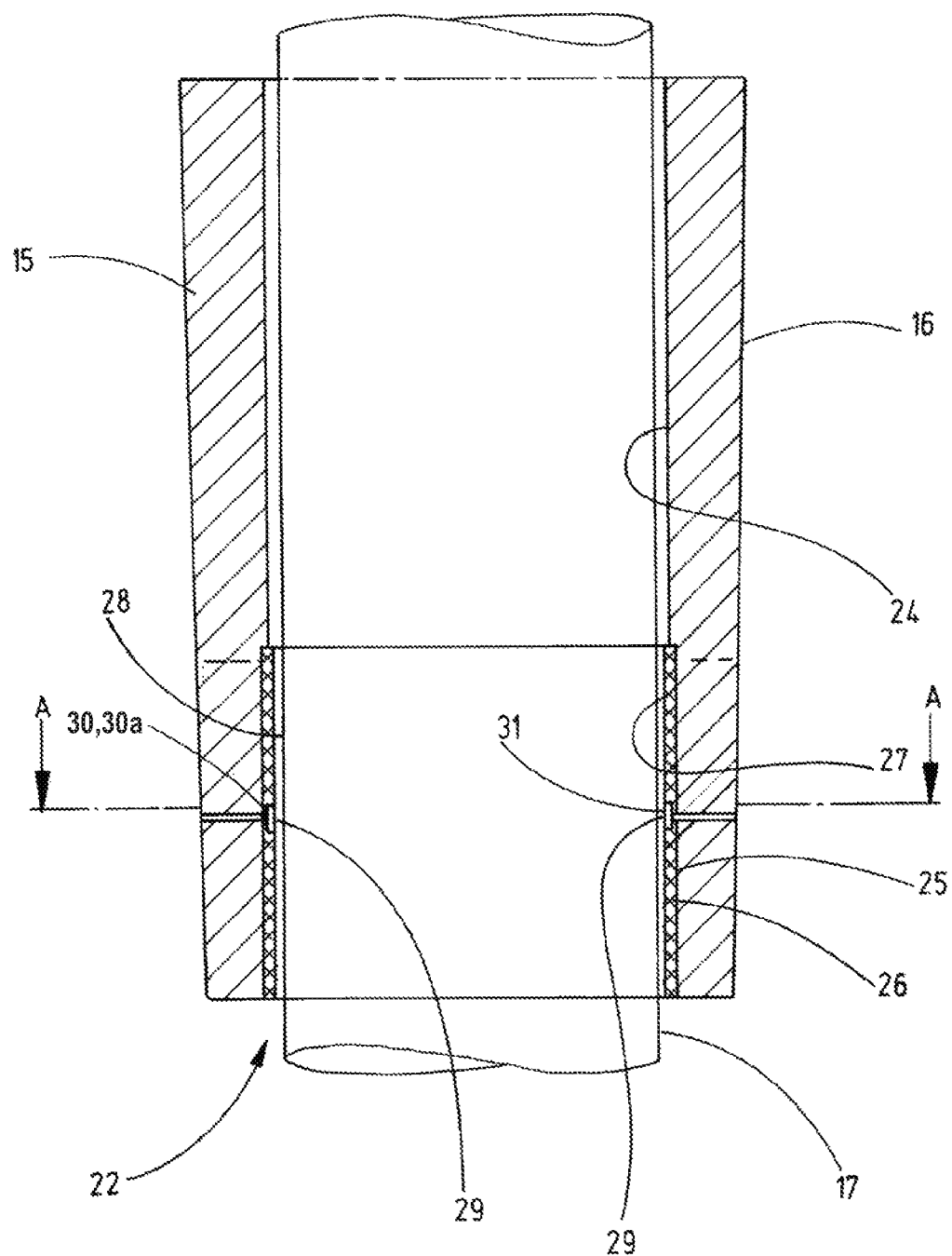
Figure 4:
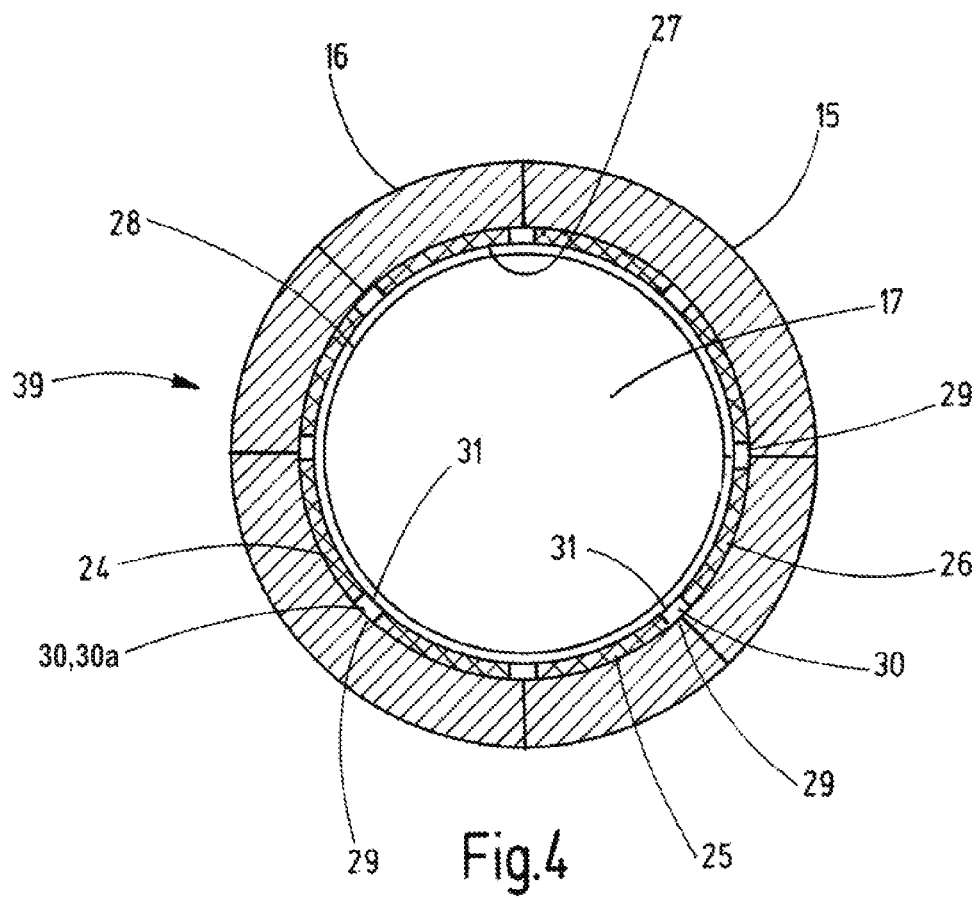
Figure 5:
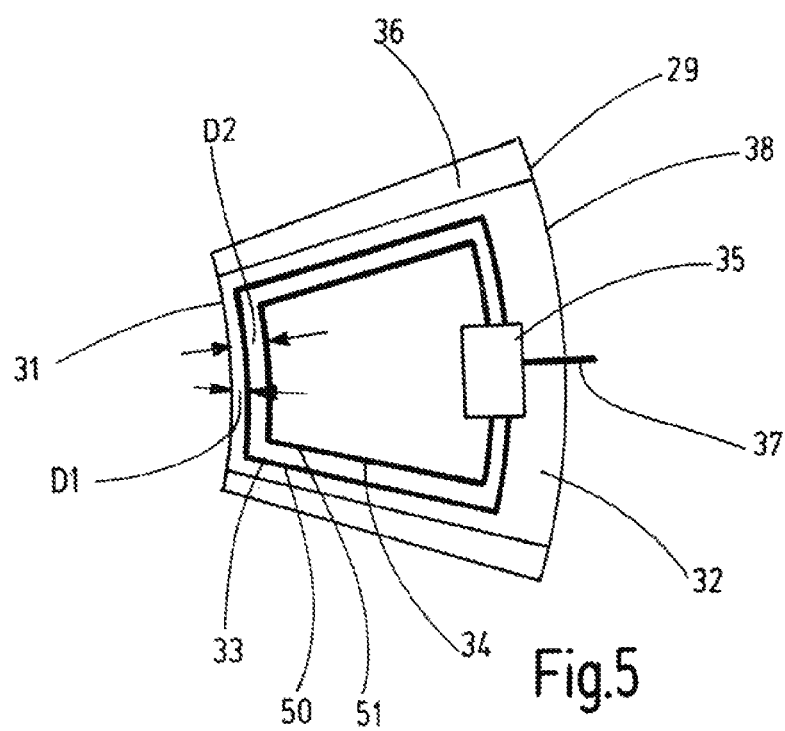
Figure 8:
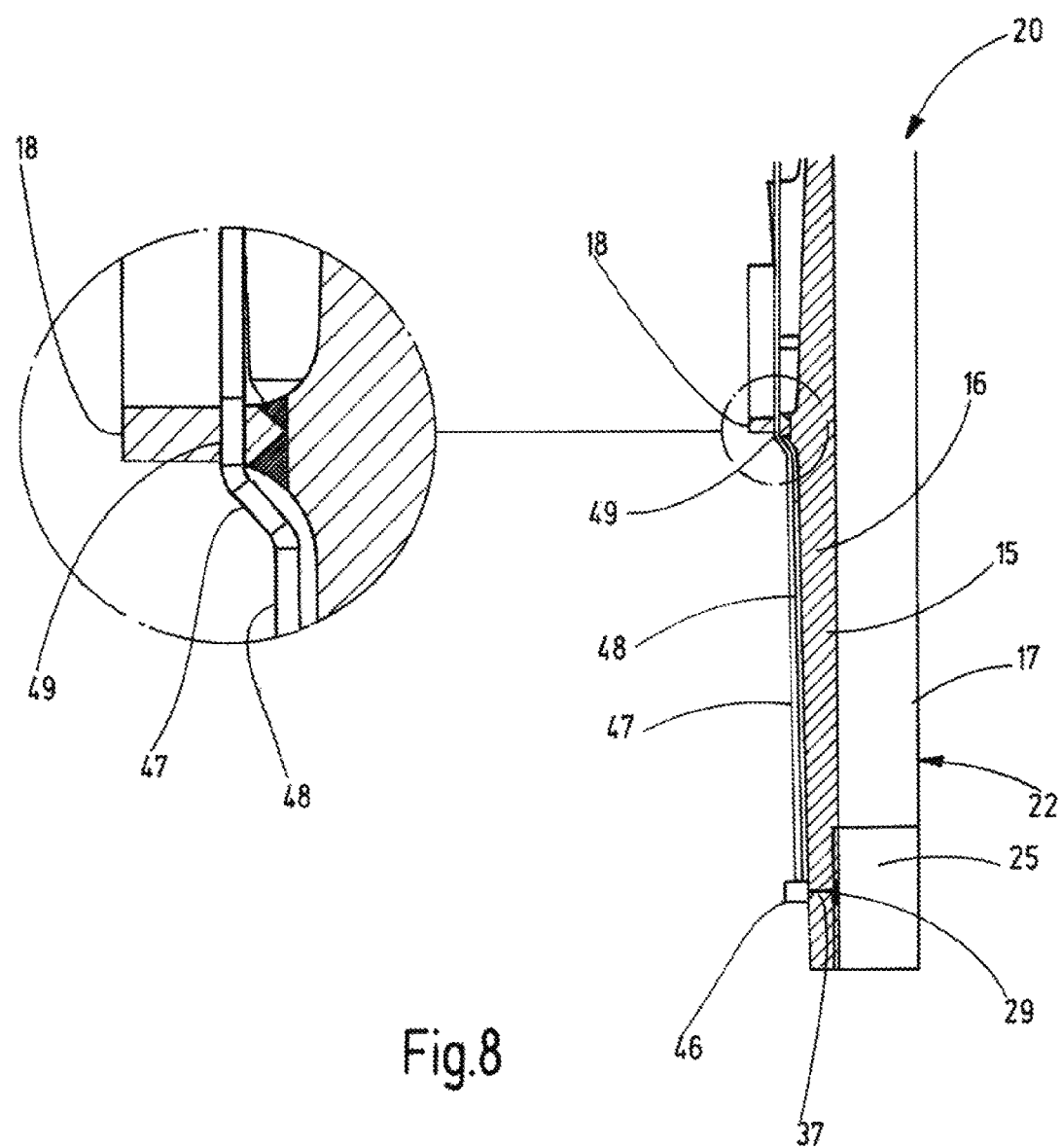
Figure 15:
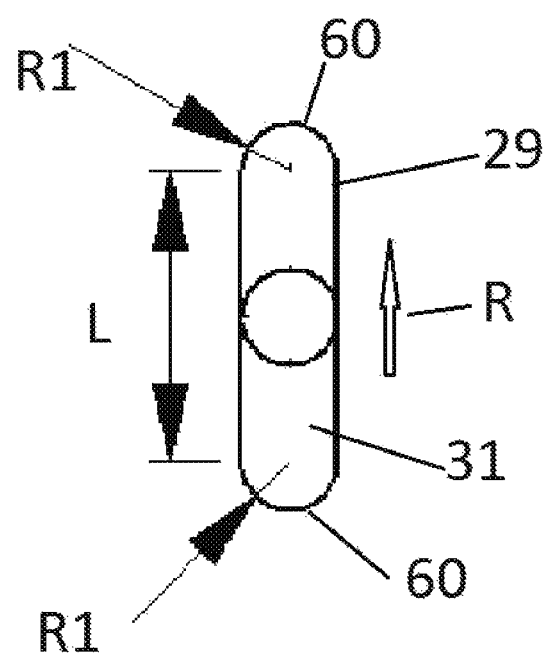

Exemplary embodiments of the invention will be explained in greater detail hereinafter on the basis of the drawings, in which:

FIG. 1 in a side view shows the stern of a ship with a bearing for supporting a rudder shaft, FIG. 2 in a rear view shows the stern of a ship with a bearing for supporting a rudder shaft, FIG. 3 in a side view shows the lower end portion of a rudder trunk and rudder shaft with a bearing, FIG. 4 in a cross-sectional view shows the lower end region of a rudder trunk and rudder shaft with a bearing, FIG. 5 shows a measurand sensor with a wear surface, FIG. 6 in a side view shows the lower end region of a rudder trunk with a bearing and a measurand sensor, FIG. 7 in a cross-sectional view shows the lower end region of a rudder trunk with a bearing and a measurand sensor, FIG. 8 in a side view shows a rudder trunk with a cable channel, FIG. 9 is a side view shows the lower end region of a rudder trunk with a bearing bush and a segmented ring, FIG. 10 in a cross-sectional view shows the lower end region of a rudder trunk with a bearing bush and a segmented ring, FIG. 11 shows a two-part bearing bush with a segmented ring, FIG. 12 shows a two-part bearing bush with a segmented ring, FIG. 13 shows a one-part bearing bush with a segmented ring, FIG. 14 shows a measurand sensor with a wear surface in a worn state, FIG. 15 shows a measurand sensor with an elongate design.

PREFERRED EMBODIMENT OF THE INVENTION

FIGS. 1 and 2 show the stern 10 of a ship 11 comprising a bearing 100 for supporting a rudder shaft in a side view and in a rear view. Behind a propeller 12, as viewed in the direction of travel, there is arranged a rudder 13 comprising a rudder blade 14. In FIG. 2 the propeller is indicated by the propeller circle K, over which the propeller blades travel. The rudder blade 14 is arranged on a rudder shaft 17 mounted rotatably in a trunk pipe 15 of a rudder trunk 16. The rudder shaft 17 is drawn deep into the rudder blade 14. The trunk pipe 15 of the rudder trunk 16 is fixedly connected to the ship's hull 18. In a vertical direction, the rudder shaft 17 is secured above the trunk pipe 15 by means of a supporting bearing 19 formed as an axial bearing. The rudder shaft 17 is connected via an upper end region 20 to a rudder engine 21. The rudder shaft 17 is supported on the trunk pipe 15 of the rudder trunk 16 via a journal bearing 23 arranged at a lower end region 22 of the rudder shaft 17. The journal bearing 23 is disposed in the peripheral direction of the rudder shaft 17 running between the rudder shaft 17 and the inner side 24 of the trunk pipe 15 of the rudder trunk 16. A further journal bearing could be provided optionally in order to support the upper end region 20 of the rudder shaft 17.

FIG. 3 shows an enlarged illustration of the rudder trunk 16 and of the lower end region 22 of the rudder shaft 17. A first bearing element 26 formed as a bearing bush 25 is arranged between the inner side 24 of the trunk pipe 15 of the rudder trunk 16 and the rudder shaft 17. The first bearing element 26 has a sliding surface 27 for contacting a second bearing element 28 in a sliding manner. The second bearing element 28 is formed in the illustrated embodiment as part of the rudder shaft 17. Measurand sensors 29 are arranged recessed in recesses 30 or measurand sensor receptacles 30a in the bearing bush 25. The measurand sensors have wear surfaces 31.

FIG. 4 shows a section through the trunk pipe 15 of the rudder trunk 16 along the line of section A-A in FIG. 3. The first bearing element 26 formed as a bearing bush 25 is arranged on the inner side 24 of the rudder trunk 16 and is arranged with the sliding surface 27 contacting the rudder shaft 17 in a sliding manner. Measurand sensors 29 are arranged in recesses 30 formed for this purpose in the bearing bush 25 at regular distances in the peripheral direction of the bearing bush 25. The measurand sensors 29 each have a wear surface 31, via which the measurand sensors 29 are arranged in contact with the rudder shaft 17 in a sliding manner. The wear surface 31 of each measurand sensor 29 extends in line or flush with the sliding surface 27 of the bearing bush 25. In particular, the wear surface 31 does not protrude radially inwardly beyond the sliding surface 27 of the bearing bush 25. In the illustrated embodiment the measurand sensors 29 are distributed at regular angular intervals over the periphery of the bearing bush 25. However, embodiments are also conceivable in which the distances are irregular.

FIG. 5 shows a cross-section through a measurand sensor 29. The measurand sensor 29 has a compact form and in particular is not elongate or pin-shaped. The measurand sensor 29 has a circuit board 32, in which a first conductor path 33 and a second conductor path 34 are integrated. However, more than two conductor paths or conductor path loops can also be provided. Furthermore, a control unit 35 is arranged on the circuit board 32 and is designed to measure the electrical resistance of the first conductor path 33 or of the second conductor path 34 and/or to determine a short circuit between the first conductor path 33 and the second conductor path 34. The first conductor path 33 has an approximately square shape and is disposed in regions at a distance D1 from the wear surface 31 of the measurand sensor 29. The second conductor path 34 likewise has an approximately square shape and is arranged in regions at a distance D2 from the wear surface 31. The second distance D2 is greater here than the first distance D1. The difference between the distances D1 and D2 is preferably between 100 μm and 1000 μm, and the distance D1 of the first conductor path 33 from the wear surface 31 is likewise between 100 μm and 1000 μm. The circuit board 32 comprising the first conductor path 33 and second conductor path 34 and also the control unit 35 is moulded in an electrically non-conductive material, such as synthetic resin 36. The control unit 35 of the measurand sensor 29 is connected to a signal line 37, which exits from the measurand sensor 29 on the side 38 opposite the wear surface 31. The control unit 35 of the measurand sensor 29 can exchange information and data via the signal line 37 with a superordinate computing unit (not illustrated) of the bearing 100 for supporting a shaft or the bearing clearance measuring device 39.

As illustrated in FIGS. 6 and 7, the recess 30 in which the measurand sensor 29 is received is formed in the manner of a slot-shaped groove 40. The groove 40 has the form of a blind bore 41, which does not fully pass through the bearing bush 25. A through-hole 43 is disposed in the bottom 42 of the blind bore 41. A drilled channel 44 is disposed in the trunk pipe 15 of the rudder trunk 16 and is oriented in the direction of the through-hole 43. The signal line 37 of the measurand sensor 29 is guided through the through-hole 43 to the outer side of the trunk pipe 15 of the rudder trunk 16. At least one cable box 46 is arranged on the outer side 45 of the rudder trunk 16, and at least one of the signal lines 37 of the measurand sensor 29 leads into said cable box. The signal lines 37 can be bundled in the cable box 46 and are guided further into a guide means formed as a cable channel 47. The measurand sensor 29 can be inserted into and/or removed from the first bearing element 26 or the bearing bush 25 only from the side of the sliding surface 27. The bottom 42 of the blind bore 41 prevents any play of the measurand sensor 29 in the radial direction of the bearing bush 25. The measurand sensor 29 for this purpose rests against the bottom 42 of the blind bore 41 formed as a contact face.

As illustrated in FIG. 8, the cable channel 47 extends on the outer side of the trunk pipe 15 of the rudder trunk 16 in the vertical direction as far as the upper end region portion 20 of the rudder shaft 17. In addition to the signal lines 37, power lines 48 for supplying power to the measurand sensors 29 and in particular to the control unit 35 arranged on the measurand sensors 29 also run through the cable channel 47. The rudder trunk 16 is fixedly welded to the ship's hull 18. A hull bore 49 is provided in the region of connection of the ship's hull 18 to the trunk pipe 15 of the rudder trunk 16, through which bore the cable channel 47 is guided into the interior of the ship's hull 18. The gap between the hull bore 49 and the cable channel 47 is sealed in a watertight manner.

The operating principle of the bearing clearance measuring device 39 will now be described with reference to FIGS. 4, 5 and 14. The measurand sensor 29 is disposed with the wear surface 31 contacting the rudder shaft 17 in a sliding manner. The surface of the rudder shaft 17 here constitutes the second bearing element 28. As a result of abrasive wear, caused by rotations of the rudder shaft 17 or deflections of the rudder 13, the wear surface 31 of the measurand sensor 29 is abraded layer by layer. As soon as a layer of a thickness corresponding to the first distance D1 of the wear surface 31 has been abraded, the first conductor path 33 is exposed or the first conductor path 33 lies in the wear surface 31. With continued wear, the first conductor path 33 is ground away and interrupted. As soon as the first conductor path 33 is interrupted, the control unit 35 on the circuit board 32 of the first measurand sensor 29 determines a sudden rise of the electrical resistance in the case of a dry bearing. With continued wear, further layers of the synthetic resin 36 of the measurand sensor 29 are rubbed off to a thickness corresponding to the second distance D2, whereupon the second conductor path 34 is also exposed or lies in the wear surface 31. With continued abrasion again, the second conductor path 34 is lastly also rubbed through, and a sudden rise of the electrical resistance of the second conductor path 34 can be determined by the control unit 35. In the case of a dry bearing 23, these jumps in the electrical resistance can be assessed as measured values for abrasion of the measurand sensor 29 and therefore for wear of the bearing bush 25. If, by contrast, a water-lubricated bearing 23 is provided, a severing of the first conductor path 33 or second conductor path 34 cannot be measured with absolute certainty on account of the conductivity of seawater, since the electrically conductive seawater takes on the task of forwarding the electrical current instead of the first conductor path 33 and the second conductor path 34.

For this purpose, the control unit 35 is designed to determine a short circuit between the first conductor path 33 and second conductor path 34. If the wear surface 31 has been abraded by a layer thickness corresponding to the second distance D2 and therefore parts of the first conductor path 33 and the second conductor path 34 are exposed, the end regions 50, 51 of the conductor paths 33, 34 come into electrical contact with one another either by direct contact or by means of the electrically conductive seawater wetting the wear surface 31 and produce a short circuit between the first conductor path 33 and the second conductor path 34. This short circuit can be determined unequivocally by the control unit 35, and the measured value, as measurand, is conducted through the signal line 37 to a superordinate computing unit, which determines the wear of the measurand sensor 29 and therefore of the bearing 23 on the basis of the measured values.

In this respect, FIG. 14 illustrates the case in which the wear surface 31 of the measurand sensor 29 has been rubbed off by abrasive wear to such an extent that the first conductor path 33 and the second conductor path 34 have been exposed or rubbed through. In other words, the wear surface 31 has receded, as a result of wear, outwardly in the radial direction in the direction of the control unit 35, by approximately the layer thickness corresponding to the second distance D2, such that the two end regions 50, 51 of the first conductor path 33 and of the second conductor path 34 lie in the wear surface 31 or border the wear surface 31 or protrude from the wear surface 31, such that the end regions 50, 51 in the case of a water-lubricated bearing come at least partially into contact with seawater wetting the wear surface 31. On account of the electrical conductivity of the seawater, a short circuit is produced between the end regions 50, 51 of the first conductor path 33 and the second conductor path 34, which can be determined by the control unit 35.

FIGS. 9 and 10 illustrate an alternative embodiment of the bearing clearance measuring device 39. The bearing clearance measuring device 39 has a segmented ring 52, which is composed of a number of ring segments 53. A ring segment 53 is formed as a sensor segment 54 and comprises a measurand sensor 29. The segmented ring 52 is arranged in a groove 55 in the bearing bush 25, said groove running around in the peripheral direction. In order to secure the sensor segment 54, clamping segments 56 are provided in the segmented ring 52 which, together with the sensor segments 54, complete the segmented ring 52.

FIGS. 11 and 12 show how the segmented ring 52 is fastened in the bearing bush 25. The bearing bush 25 is for this purpose embodied in two parts and has a first bearing part 57 and a second bearing part 58. The first bearing part 57 and the second bearing part 58 each have, in regions facing toward one another, an L-shaped profile 59 running around in the peripheral direction, which, when the first bearing part 57 and second bearing part 58 are arranged with one another, form an annular groove 55 running around the bearing bush 25 in the peripheral direction. The segmented ring 52 is arranged in the L-shaped profile 59 of the first bearing part 57 and is connected thereto in a watertight manner. The second bearing part 58 is then arranged on the first bearing part 57 in such a way that the segmented ring 52 is arranged in the L-shaped profile 59 of the second bearing part 58. As a result of this arrangement of the first and second bearing part 57, 58, the L-shaped profiles 59 of the first bearing part 57 and the second bearing part 58 together form a groove 55 running around the bearing bush 25 in the peripheral direction, in which groove the segmented ring 52 comprising sensor segments 54 and clamping segments 56 is arranged. The bearing bush 25 can be arranged in the rudder trunk 16 for example by freezing.

FIG. 13 shows a further embodiment of the bearing clearance measuring device 39. In the illustrated embodiment the bearing bush 25 is formed in one part and at one end has an L-shaped profile 59 running around in the peripheral direction, in which the segmented ring 52 can be arranged. In this embodiment the segmented ring 52 comprising the measurand sensor 29 is thus disposed above or below the bearing bush 25 and not centrally in the bearing bush 25 as considered in the axial direction.

FIG. 15 shows a measurand sensor 29 with a substantially elongate design. A wear surface 31 of the measurand sensor 29 is not arranged on one of the end faces 60, or is not arranged on one of the sides, outer sides or planes perpendicular to the direction R of the elongated design. In the embodiment of the measurand sensor 29 according to FIG. 15, this recorder is particularly suitable for being inserted into a measurand sensor receptacle 30a or a recess 30 in the form of a slot-shaped or elongate blind bore 41 or groove 40 or channel or step preferably arranged in the sliding surface 27 in the longitudinal direction of the first bearing element 26. The end faces 60 of the measurand sensor 29 have a rounded course with a radius of curvature R1. The radius of curvature can preferably be between 2 and 20 mm, particularly preferably between 5 and 10 mm. The length L of the measurand sensor 29 in the direction R of the elongate design between the rounded end faces 60 is preferably between 20 and 40 mm, particularly preferably approximately 30 mm. The measurand sensor 29 of FIG. 15 is otherwise identical to the previously described measurand sensors and can also be used in particular in any of the devices shown in FIGS. 2 to 14.

The invention claimed is:

1. A bearing for supporting a rudder shaft or a rudder blade, comprising a first bearing element and a second bearing element, wherein the first bearing element has a sliding surface for contacting the second bearing element in a sliding manner, and at least one measurand sensor having a wear surface for contacting the second bearing element in a sliding manner,
   wherein the at least one measurand sensor is not pin-shaped.

2. The bearing according to claim 1,
   wherein the wear surface of the measurand sensor is formed in a manner corresponding to a portion of the lateral surface of a cylinder or a cone.

3. The bearing according to claim 1 or claim 2,
   wherein a measurand sensor receptacle or a recess is arranged in the sliding surface of the first bearing element, wherein the at least one measurand sensor is arranged in the measurand sensor receptacle or the recess, and in that the measurand sensor can be inserted into the measurand sensor receptacle and/or can be removed from the measurand sensor receptacle exclusively from the side of the sliding surface.

4. The bearing according to claim 1,
   wherein the first bearing element is a bearing bush, and/or wherein the first bearing element can be arranged on the inner side of a trunk pipe of a rudder trunk, and/or wherein the first bearing element can be arranged on the outer side of the trunk pipe of the rudder trunk, and/or wherein the second bearing element can be arranged on a rudder shaft or can be formed as part of a rudder shaft, and/or wherein the second bearing element can be arranged on a rudder blade of a rudder, and/or wherein the bearing can be arranged between the trunk pipe and the rudder shaft, and/or wherein the bearing can be arranged between the trunk pipe and the rudder blade.

5. The bearing according to claim 1,
   wherein the measurand sensor has an electrically conductive material, wherein the electrically conductive material is arranged in the region of the wear surface in order to measure the wear of the measurand sensor.

6. The bearing according to claim 5,
wherein the electrically conductive material is formed as at least two layers and/or is formed as at least two conductor circuits and/or as at least two conductor paths, wherein, in an unworn state of the measurand sensor, the at least two layers or conductor layers and/or the at least two conductor circuits and/or the at least two conductor paths are electrically insulated from each other.

7. The bearing according to claim 6,
wherein the at least two layers or conductor layers and/or conductor circuits and/or conductor paths are arranged at a different distance from the wear surface, and/or wherein the at least two layers or conductor layers and/or conductor circuits and/or conductor paths are arranged adjacently to each other.

8. The bearing according to claim 5,
wherein the measurand sensor comprises a control unit, wherein the control unit is designed to detect wear of the measurand sensor by measuring the change in electrical resistance and/or by measuring a short circuit between two layers and/or conductor circuits and/or conductor paths which are electrically insulated from one another in the unworn state of the measurand sensor.

9. The bearing according to claim 5,
wherein the electrically conductive material is arranged in a carrier, and/or wherein the electrically conductive material and/or the carrier is arranged or molded in a non-metal material.

10. The bearing according to claim 3,
wherein an opening passing through the first and/or the second bearing element is formed in a wall and/or side wall of the measurand sensor receptacle or of the recess, and wherein a signal conduction means, of the measurand sensor is guided through the opening.

11. A bearing clearance measuring device for measuring the bearing clearance of a bearing of a rudder shaft or of a rudder blade, comprising a bearing for supporting a rudder shaft, or a rudder blade, said bearing comprising a first bearing element and a second bearing element, wherein the first bearing element has a sliding surface for contacting the second bearing element in a sliding manner, and said bearing comprising at least one measurand sensor having a wear surface for contacting the second bearing element in a sliding manner,
wherein the at least one measurand sensor is not pin-shaped,
wherein the bearing clearance measuring device comprises a computing unit which is designed to receive and to process signals and/or information of the at least one measurand sensor.

12. A rudder for a ship comprising a rudder shaft and a rudder blade arranged on the rudder shaft,
wherein the rudder comprises a bearing for supporting the rudder shaft or the rudder blade, comprising a first bearing element and a second bearing element, wherein the first bearing element has a sliding surface for contacting the second bearing element in a sliding manner, and at least one measurand sensor having a wear surface for contacting the second bearing element in a sliding manner, wherein the at least one measurand sensor is not pin-shaped, and/or
wherein the rudder comprises a bearing clearance measuring device for measuring the bearing clearance of a bearing of a rudder shaft or of a rudder blade, comprising a bearing for supporting a rudder shaft or a rudder blade, said bearing comprising a first bearing element and a second bearing element, wherein the first bearing element has a sliding surface for contacting the second bearing element in a sliding manner, and said bearing comprising at least one measurand sensor having a wear surface for contacting the second bearing element in a sliding manner, wherein the at least one measurand sensor is not pin-shaped, wherein the bearing clearance measuring device comprises a computing unit which is designed to receive and to process signals and/or information of the at least one measurand sensor.

13. The rudder according to claim 12,
wherein the rudder has a rudder trunk comprising a trunk pipe, wherein the bearing is arranged between the trunk pipe and the rudder shaft, and/or wherein the bearing is arranged between the trunk pipe and the rudder blade, and/or wherein the trunk pipe has a guide means on the outside or the inner side and wherein a signal conduction means of the measurand sensor is arranged in the guide means in such a way that signals and/or information can be conducted or transferred between the measurand sensor and a computing unit.

14. The rudder according to claim 13,
wherein a spacer is provided, wherein the spacer can be attached to the inner side of the trunk pipe, such that damage to the measurand sensor during insertion of the rudder shaft into the trunk pipe of the rudder trunk can be avoided.

15. A method for measuring a bearing clearance and/or a wear of a bearing for a rudder shaft, or for a rudder blade,
wherein at least one non-pin-shaped measurand sensor having at least two layers and/or conductor circuits and/or conductor tracks made of an electrically conductive material is arranged in a bearing for supporting a rudder shaft, or a rudder blade, wherein the electrical resistance of the at least two layers and/or conductor circuits and/or conductor paths is measured, and wherein a bearing clearance and/or a wear of the bearing is determined when a change in the electrical resistance at least of one of the two layers and/or conductor circuits and/or conductor paths is measured, and/or wherein a bearing clearance and/or wear is determined when a short circuit between two of the layers and/or conductor circuits and/or conductor paths is measured.

16. The method according to claim 15,
wherein measured values and/or jumps in the measured values of the electrical resistance and/or a short circuit are stored, and/or wherein at least one layer and/or a conductor circuit and/or a conductor path made of an electrically conductive material is severed before the measurand sensor is arranged in the bearing, and wherein a reference measurement and/or test measurement of the electrical resistance and/or a short circuit is taken.

17. The bearing according to claim 5, wherein the electrically conductive material is formed as at least one layer or conductor layer and/or at least one conductor circuit and/or at least one conductor path.

18. The bearing according to claim 7, wherein the conductor paths are arranged adjacently to each other at a distance of 100 µm to 1000 µm.

19. The bearing according to claim 9, wherein the carrier is a circuit board or a printed circuit board.

20. The bearing according to claim 10, wherein the signal conduction means is an electrical line or cable.

* * * * *